US012195220B2

(12) United States Patent
Koike

(10) Patent No.: US 12,195,220 B2
(45) Date of Patent: Jan. 14, 2025

(54) DRUG DISCHARGE DEVICE AND CONTROL METHOD FOR DRUG DISCHARGE DEVICE

(71) Applicant: YUYAMA MFG. CO., LTD., Osaka (JP)

(72) Inventor: Naoki Koike, Osaka (JP)

(73) Assignee: Yuyama Mfg. Co., Ltd., Osaka (JP)

( * ) Notice: Subject to any disclaimer, the term of this patent is extended or adjusted under 35 U.S.C. 154(b) by 134 days.

(21) Appl. No.: 17/996,026

(22) PCT Filed: Apr. 9, 2021

(86) PCT No.: PCT/JP2021/015095
§ 371 (c)(1),
(2) Date: Oct. 12, 2022

(87) PCT Pub. No.: WO2021/210516
PCT Pub. Date: Oct. 21, 2021

(65) Prior Publication Data
US 2023/0192333 A1   Jun. 22, 2023

(30) Foreign Application Priority Data
Apr. 17, 2020   (JP) .................................. 2020-073984

(51) Int. Cl.
*B65B 5/10*          (2006.01)
*B65B 57/14*         (2006.01)
(Continued)

(52) U.S. Cl.
CPC .............. *B65B 5/103* (2013.01); *B65B 57/14* (2013.01); *B65B 59/02* (2013.01); *B65G 1/1376* (2013.01); *B65B 2230/02* (2013.01)

(58) Field of Classification Search
CPC .. B65B 5/103; B65B 1/30; B65B 9/06; B65B 9/04; B65B 47/02; B65B 47/04
(Continued)

(56) References Cited

U.S. PATENT DOCUMENTS

| 7,293,672 B2 | 11/2007 | Mori et al. |
| 2003/0057231 A1 | 3/2003 | Kim |

(Continued)

FOREIGN PATENT DOCUMENTS

| CA | 2191900 A1 | 6/1998 |
| CA | 2217220 A1 | 6/1998 |

(Continued)

OTHER PUBLICATIONS

WIPO, Japanese International Search Authority, International Search Report (with English translation) and Written Opinion mailed on May 11, 2021 in International Patent Application No. PCT/JP2021/015095, 9 pages.

(Continued)

*Primary Examiner* — Jacob A Smith
(74) *Attorney, Agent, or Firm* — Masuvalley & Partners

(57) ABSTRACT

To provide a drug discharge device capable of reducing complexity when distributing a drug into a manual distribution device. A drug discharge device includes a manual distribution member 15 that includes a plurality of recessed portions 20 in which a solid drug is distributed, discharge means that discharges the drug distributed in the recessed portions 20 to a downstream side directly or via another member, and a control device that controls the discharge means, in which the discharge means is capable of individually discharging a drug corresponding to a predetermined recessed portion 20, the control device assigns the same drug to the recessed portions 20 in adjacent regions based on prescription information including information on a drug to (Continued)

be provided to a plurality of patients or one patient, and the discharge means discharges the drugs in a predetermined order.

11 Claims, 25 Drawing Sheets

(51) Int. Cl.
 *B65B 59/02* (2006.01)
 *B65G 1/137* (2006.01)
(58) Field of Classification Search
 USPC .......................................................... 53/246
 See application file for complete search history.

(56) References Cited

U.S. PATENT DOCUMENTS

| 2009/0152291 | A1* | 6/2009 | Ohmura | G07F 17/0092 221/197 |
|---|---|---|---|---|
| 2013/0212987 | A1 | 8/2013 | Shigeyama et al. | |
| 2015/0066204 | A1 | 3/2015 | Patel et al. | |
| 2018/0177682 | A1 | 6/2018 | Tanaka | |
| 2019/0269576 | A1 | 9/2019 | Grosfils et al. | |

FOREIGN PATENT DOCUMENTS

| EP | 2206649 | A1 | * | 7/2010 | ............. B65B 5/103 |
|---|---|---|---|---|---|
| JP | H02-269621 | A | | 11/1990 | |
| JP | H10-119902 | A | | 5/1998 | |
| JP | H10-323382 | A | | 12/1998 | |
| JP | 2001335002 | A | * | 12/2001 | ............... B65B 1/30 |
| JP | 2007-297066 | A | | 11/2007 | |
| WO | 2007/091375 | A1 | | 8/2007 | |
| WO | 2016/136523 | A1 | | 9/2016 | |
| WO | 2017/119276 | A1 | | 7/2017 | |

OTHER PUBLICATIONS

Japan Patent Office, Office Action dated Jun. 6, 2024 in Japanese Patent Application No. 2022-515359, 9 pages.
European Patent Office, Extended European Search Report dated Apr. 5, 2024 in European Patent Application No. 21788433.7, 10 pages.

* cited by examiner

FIG. 4

| | 6 | 5 | 4 | 3 | 2 | 1 | |
|---|---|---|---|---|---|---|---|
| | A 6 | A 5 | A 4 | A 3 | A 2 | A 1 | 1 |
| | A 12 | A 11 | A 10 | A 9 | A 8 | A 7 | 2 |
| | A 18 | A 17 | A 16 | A 15 | A 14 | A 13 | 3 |
| | A 24 | A 23 | A 22 | A 21 | A 20 | A 19 | 4 |
| 10 ROWS | B 30 | B 29 | B 28 | B 27 | B 26 | A 25 | 5 |
| | B 36 | B 35 | B 34 | B 33 | B 32 | B 31 | 6 |
| | B 42 | B 41 | B 40 | B 39 | B 38 | B 37 | 7 |
| | C 48 | C 47 | C 46 | B 45 | B 44 | B 43 | 8 |
| | C 54 | C 53 | C 52 | C 51 | C 50 | C 49 | 9 |
| | D 60 | D 59 | D 58 | D 57 | D 56 | C 55 | 10 |

6 COLUMNS

FIG. 5

| PATIENT \ DOSING TIME | MORNING | NOON | EVENING | BEFORE GOING TO BED |
|---|---|---|---|---|
| a | A | | | |
| b | | B | | |
| c | | A | | |
| d | B | | | |
| e | C | | | |
| f | A | | | |
| g | B | A | | |
| h | | C | | |
| i | A | | B | |
| j | | | | D |

FIG. 6
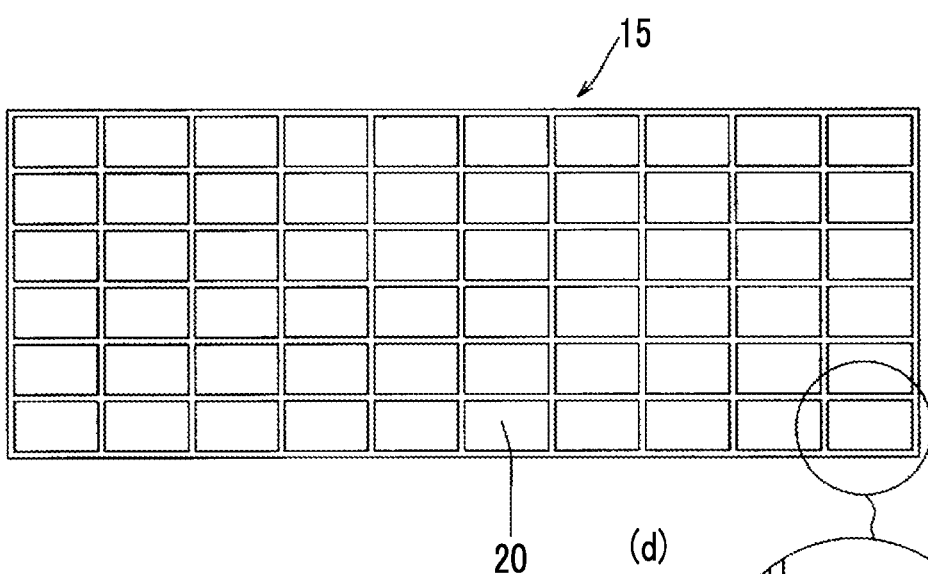
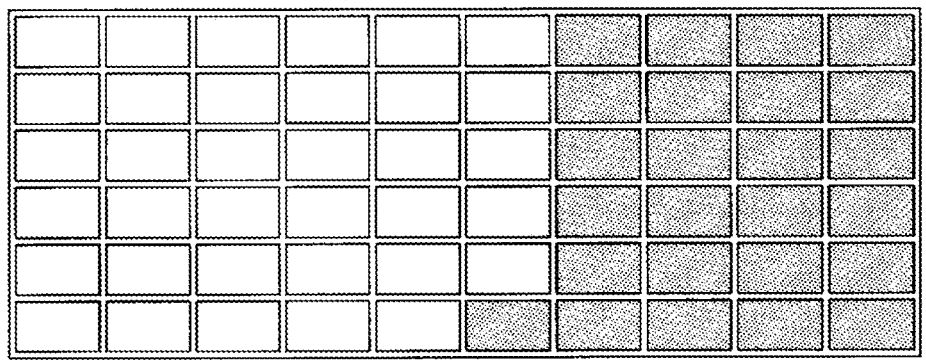
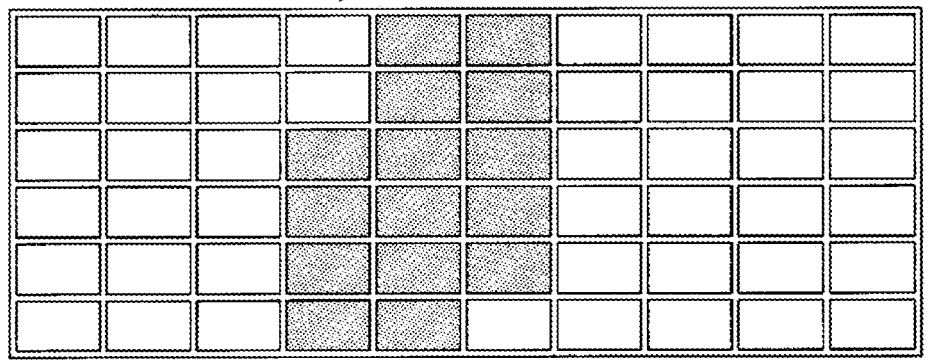

FIG. 8
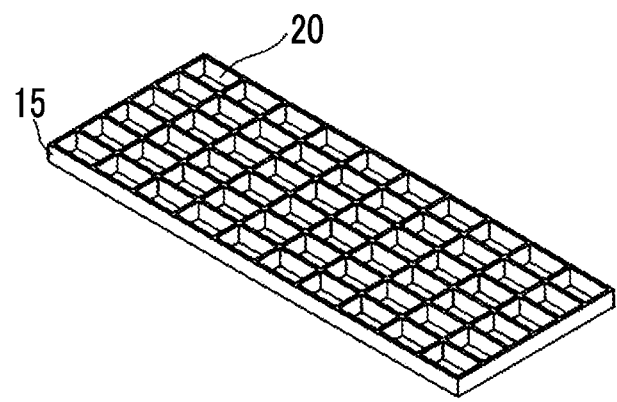
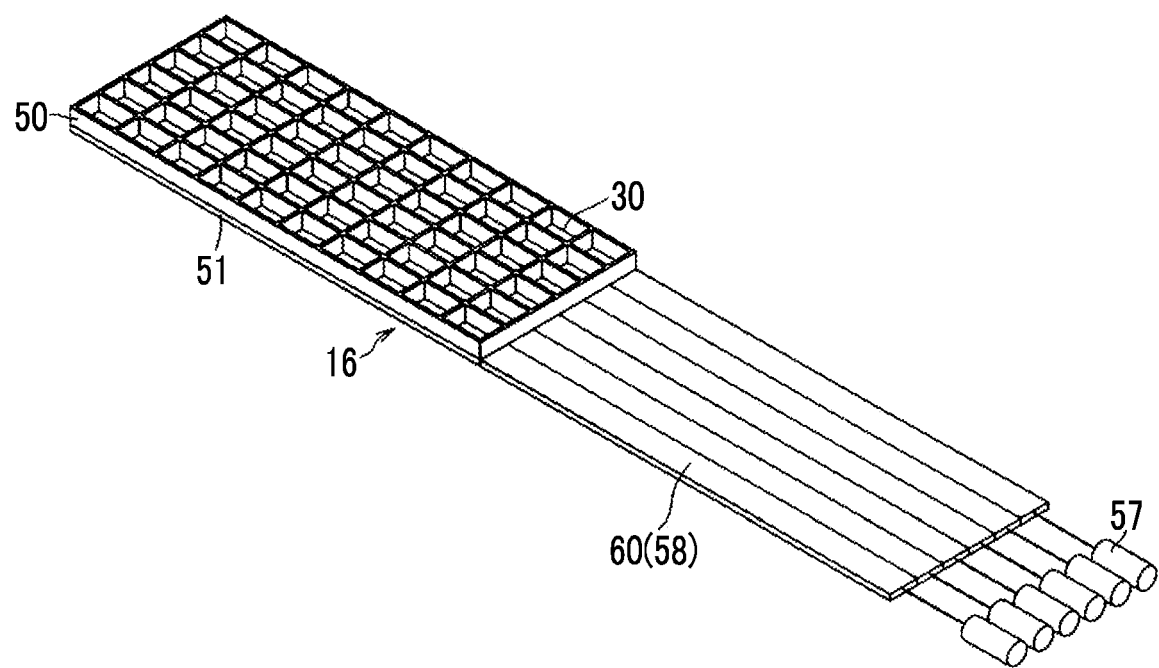

FIG. 9
(a)
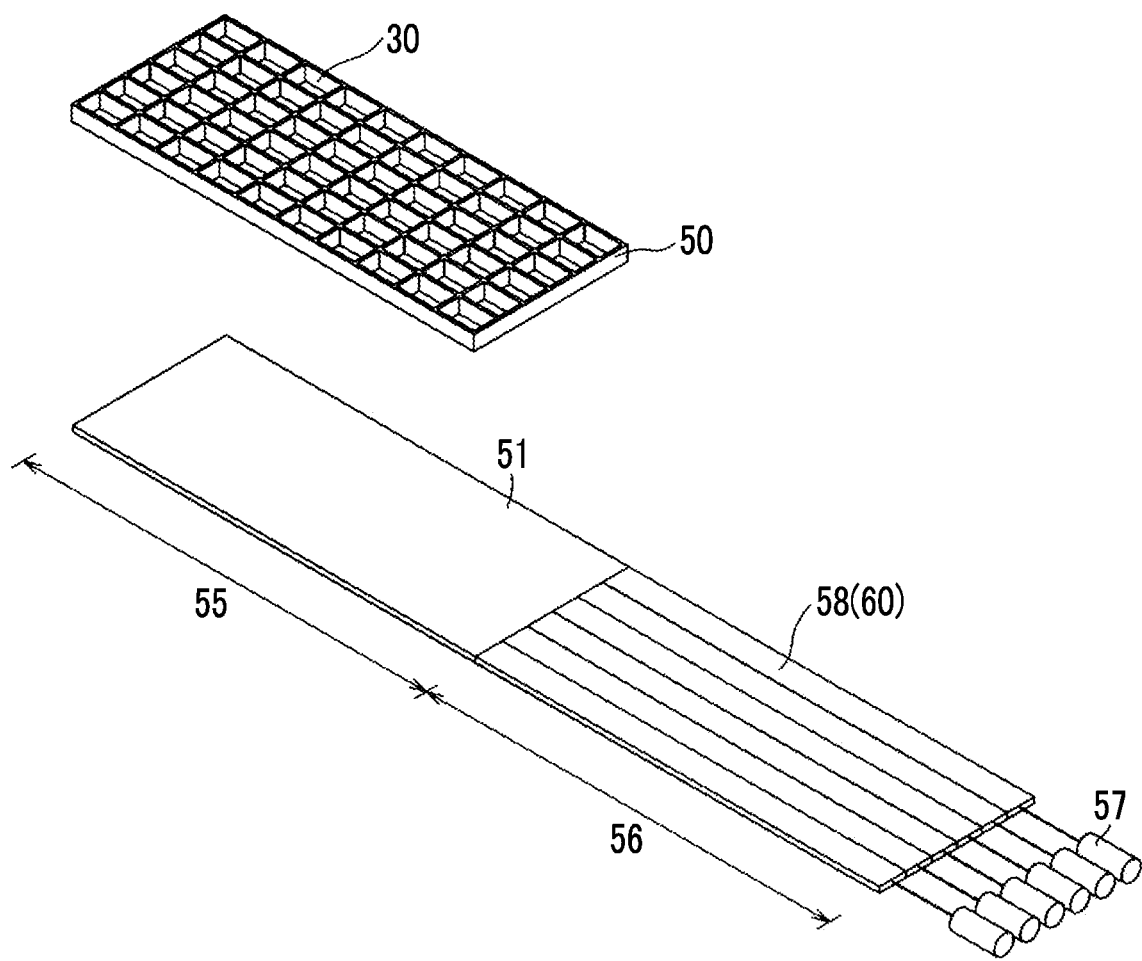
(b)
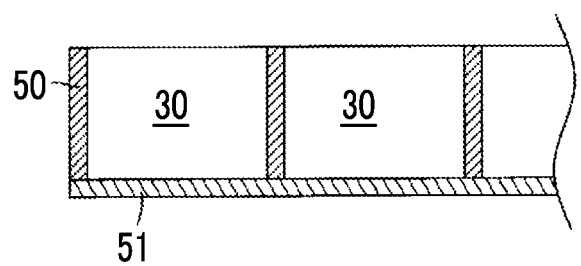

FIG. 12
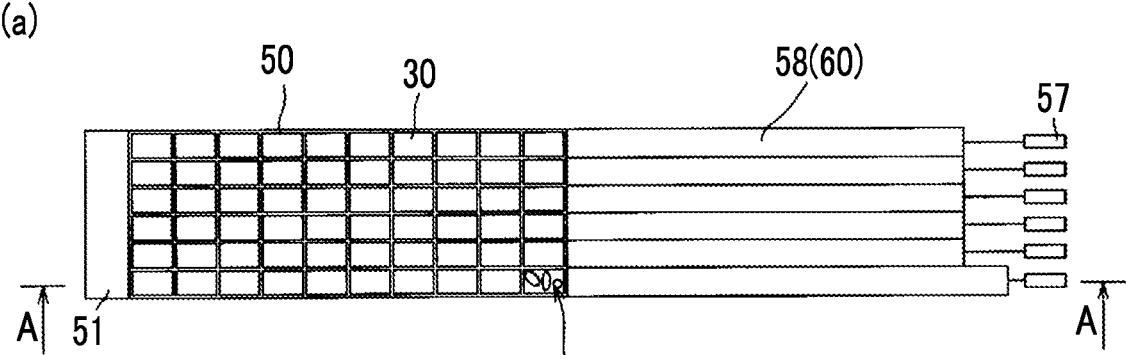
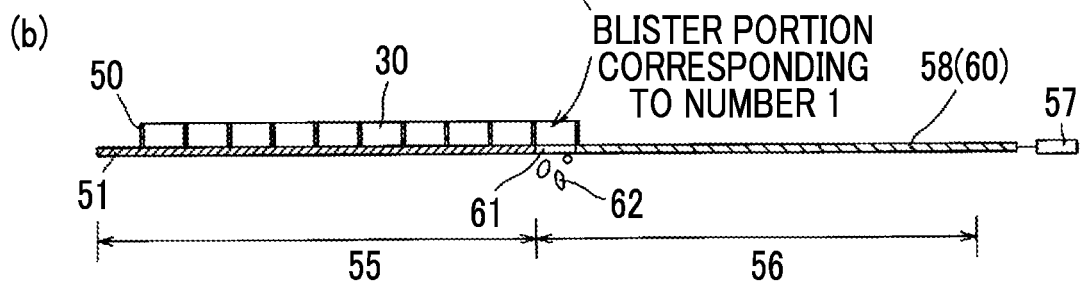
FIG. 13
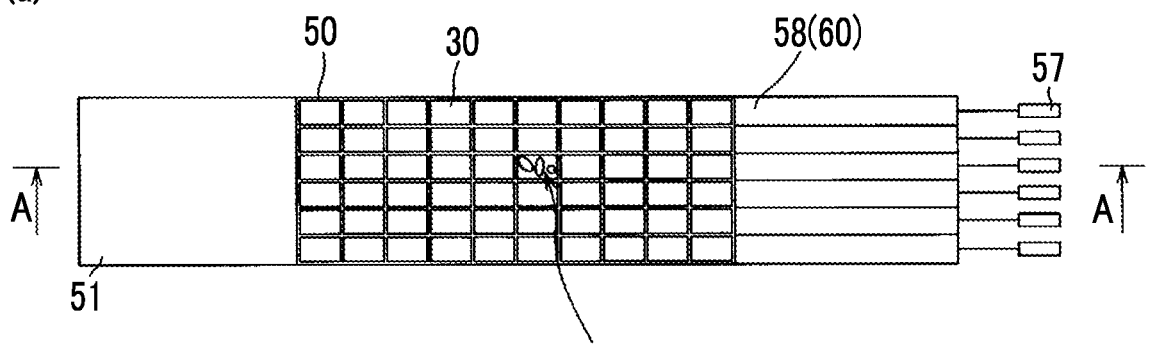
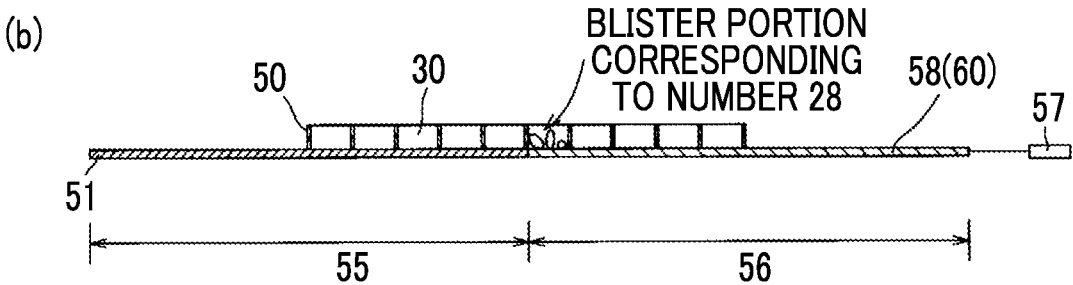

FIG. 14
(a)
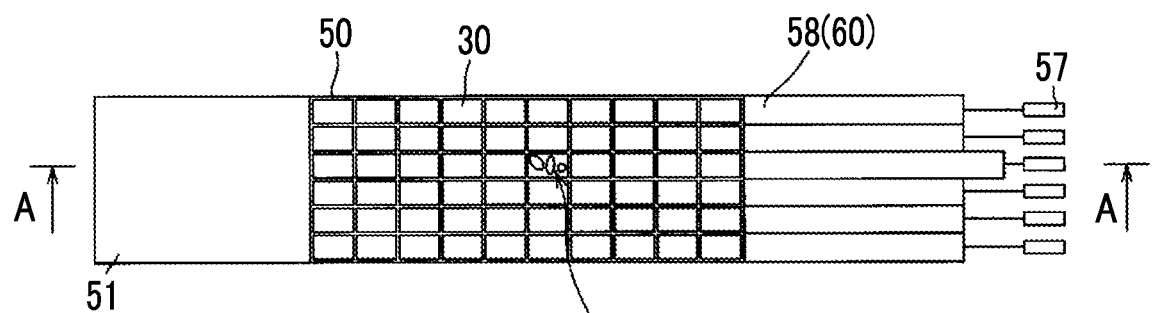
(b)
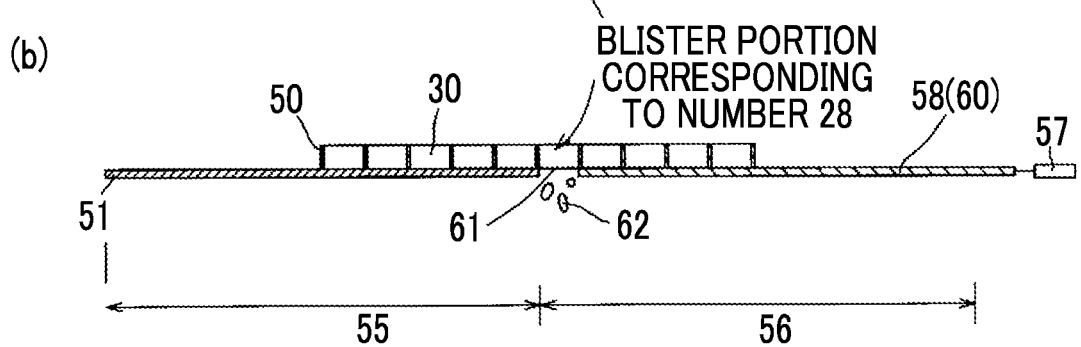

Figure 16:
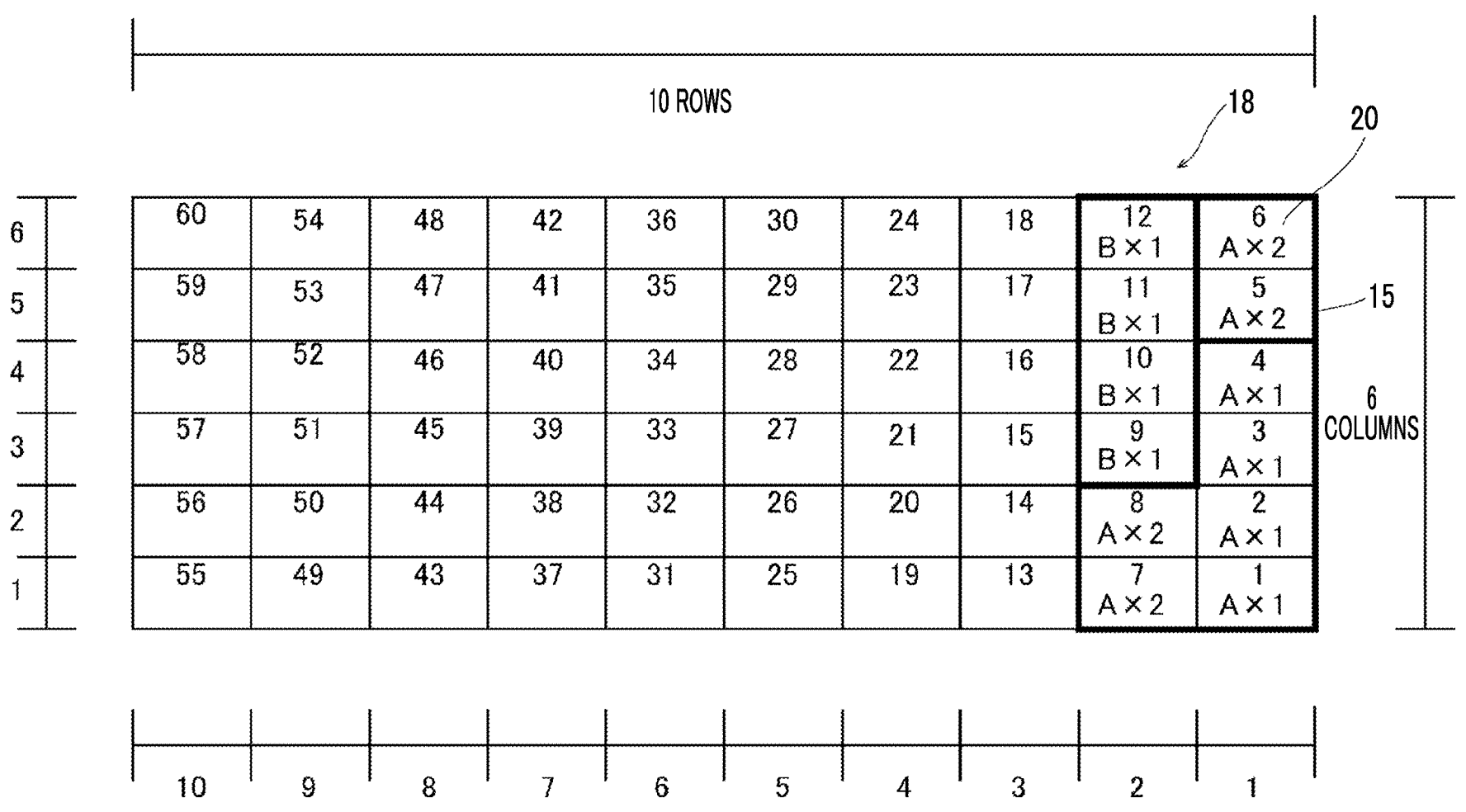

| | 6 | 5 | 4 | 3 | 2 | 1 |
|---|---|---|---|---|---|---|
| 1 | 6 Ax2 | 5 Ax2 | 4 Ax1 | 3 Ax1 | 2 Ax1 | 1 Ax1 |
| 2 | 12 Bx1 | 11 Bx1 | 10 Bx1 | 9 Bx1 | 8 Ax2 | 7 Ax2 |
| 3 | 18 | 17 | 16 | 15 | 14 | 13 |
| 4 | 24 | 23 | 22 | 21 | 20 | 19 |
| 5 | 30 | 29 | 28 | 27 | 26 | 25 |
| 6 | 36 | 35 | 34 | 33 | 32 | 31 |
| 7 | 42 | 41 | 40 | 39 | 38 | 37 |
| 8 | 48 | 47 | 46 | 45 | 44 | 43 |
| 9 | 54 | 53 | 52 | 51 | 50 | 49 |
| 10 | 60 | 59 | 58 | 57 | 56 | 55 |

6 COLUMNS

10 ROWS

FIG. 17

| | 6 | 5 | 4 | 3 | 2 | 1 |
|---|---|---|---|---|---|---|
| 1 | 6 A×1 | 5 A×1 | 4 A×1 | 3 A×1 | 2 A×1 | 1 A×1 |
| 2 | 12 A×2 | 11 A×2 | 10 A×2 | 9 A×2 | 8 A×1 | 7 A×1 |
| 3 | 18 B×1 | 17 B×1 | 16 A×2 | 15 A×2 | 14 A×2 | 13 A×2 |
| 4 | 24 B×1 | 23 B×1 | 22 B×1 | 21 B×1 | 20 B×1 | 19 B×1 |
| 5 | 30 | 29 | 28 | 27 | 26 | 25 |
| 6 | 36 | 35 | 34 | 33 | 32 | 31 |
| 7 | 42 | 41 | 40 | 39 | 38 | 37 |
| 8 | 48 | 47 | 46 | 45 | 44 | 43 |
| 9 | 54 | 53 | 52 | 51 | 50 | 49 |
| 10 | 60 | 59 | 58 | 57 | 56 | 55 |

6 COLUMNS — 15
20
18
10 ROWS

FIG. 18

| | 6 | 5 | 4 | 3 | 2 | 1 | COLUMNS |
|---|---|---|---|---|---|---|---|
| 1 | 6 A×1 B×1 | 5 A×1 B×1 | 4 A×1 B×1 | 3 A×1 B×1 | 2 A×1 B×1 | 1 A×1 B×1 | |
| 2 | 12 A×2 | 11 A×2 | 10 A×2 | 9 A×2 | 8 A×1 B×1 | 7 A×1 B×1 | |
| 3 | 18 B×1 | 17 B×1 | 16 A×2 | 15 A×2 | 14 A×2 | 13 A×2 | |
| 4 | 24 B×1 | 23 B×1 | 22 B×1 | 21 B×1 | 20 B×1 | 19 B×1 | |
| 5 | 30 | 29 | 28 | 27 | 26 | 25 | |
| 6 | 36 | 35 | 34 | 33 | 32 | 31 | |
| 7 | 42 | 41 | 40 | 39 | 38 | 37 | |
| 8 | 48 | 47 | 46 | 45 | 44 | 43 | |
| 9 | 54 | 53 | 52 | 51 | 50 | 49 | |
| 10 | 60 | 59 | 58 | 57 | 56 | 55 | |

10 ROWS

FIG. 19

FIG. 20
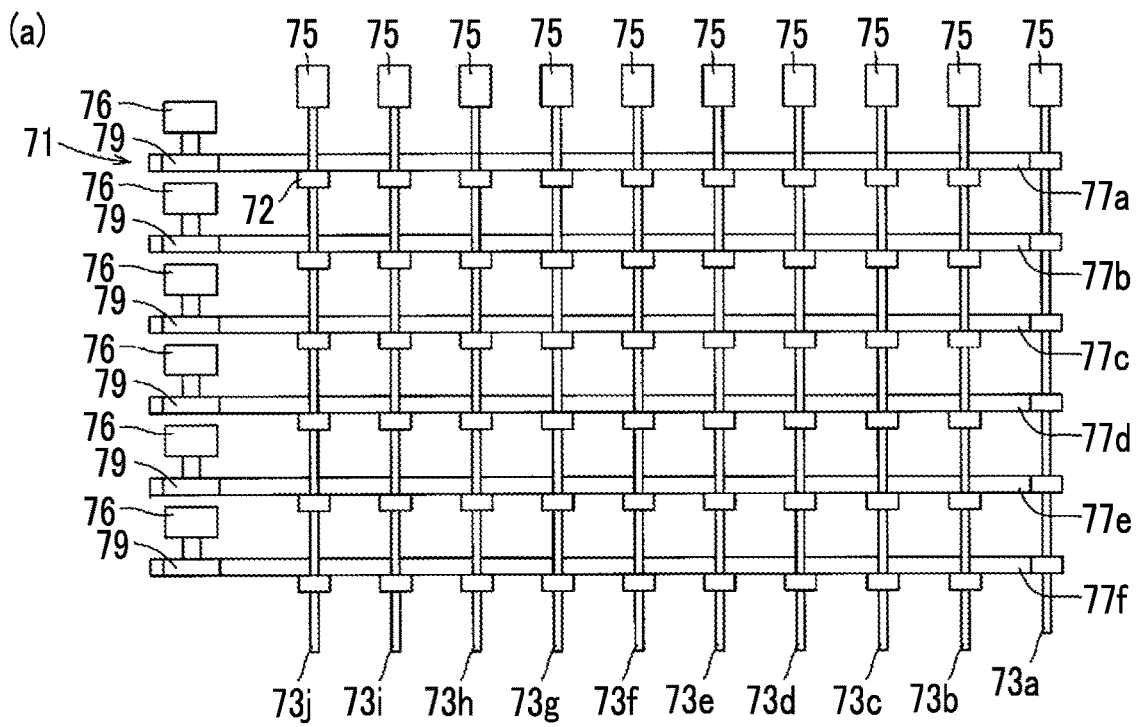
(a)
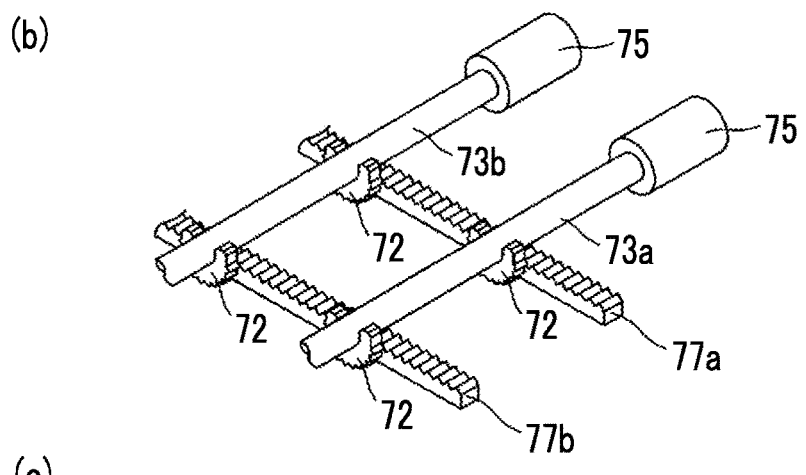
(b)
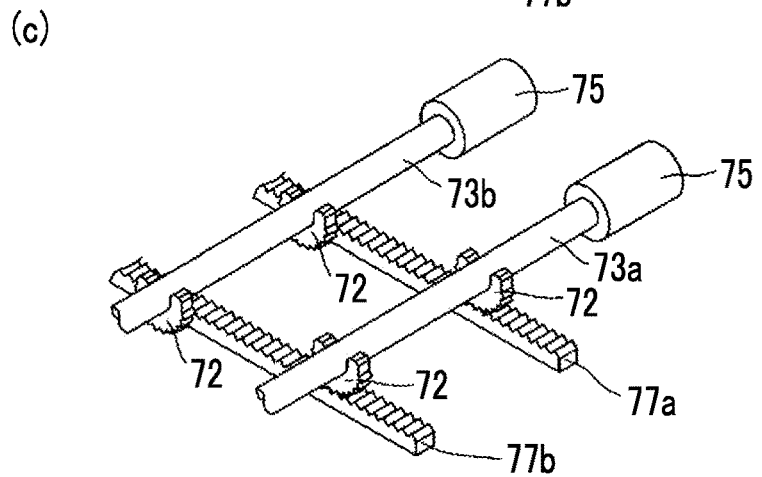
(c)

FIG. 21
(a)
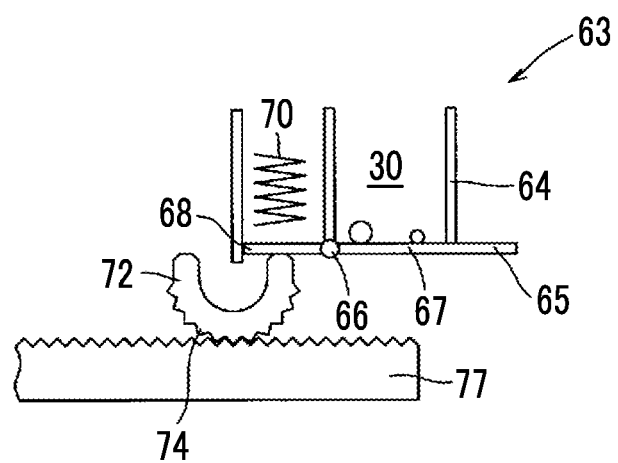
(b)
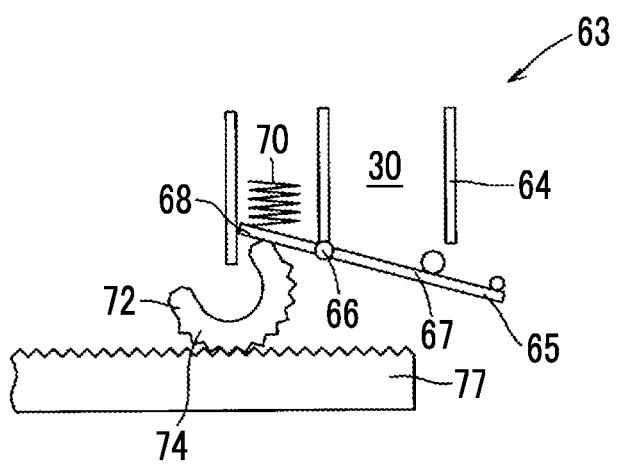

FIG. 22
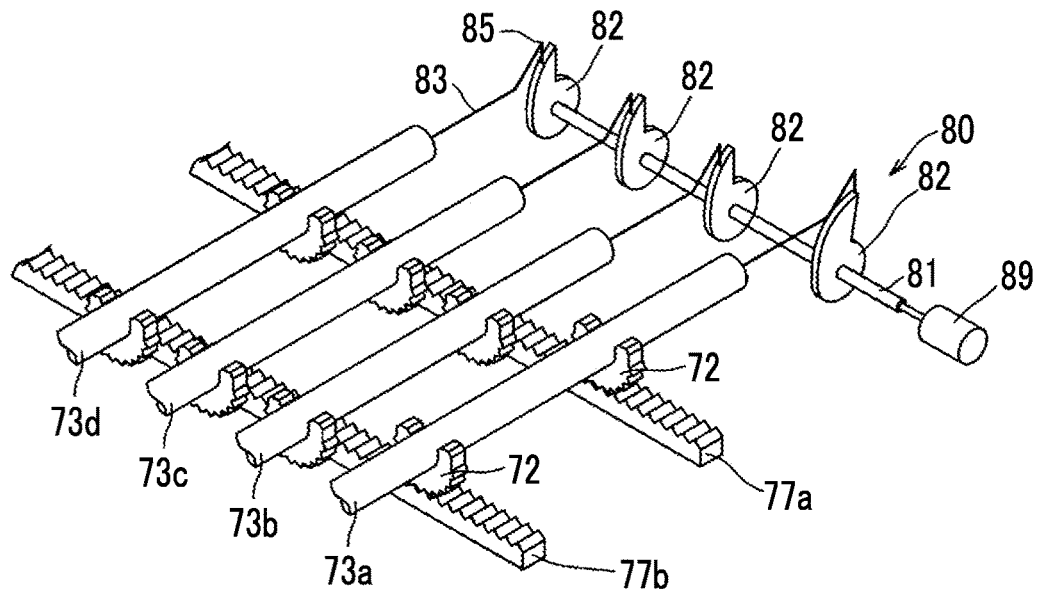
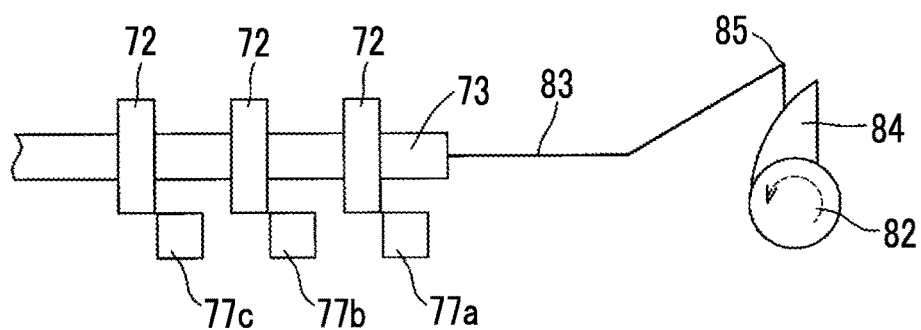
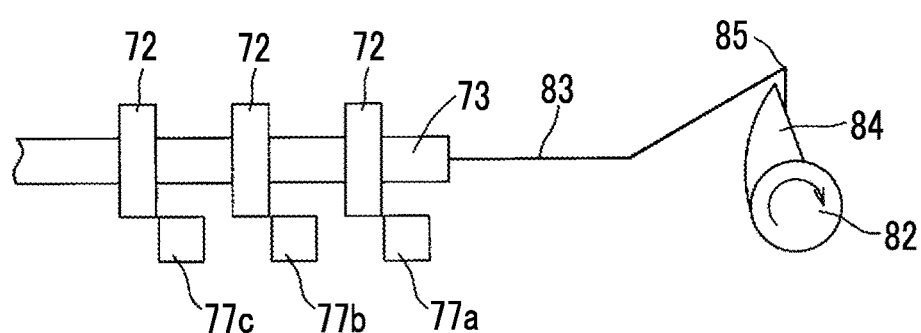
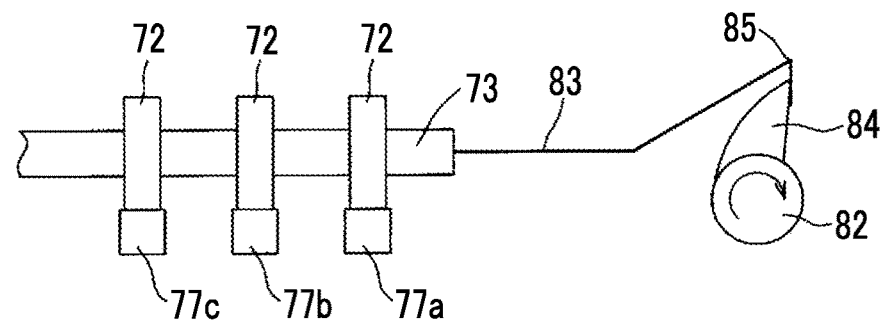

FIG. 23
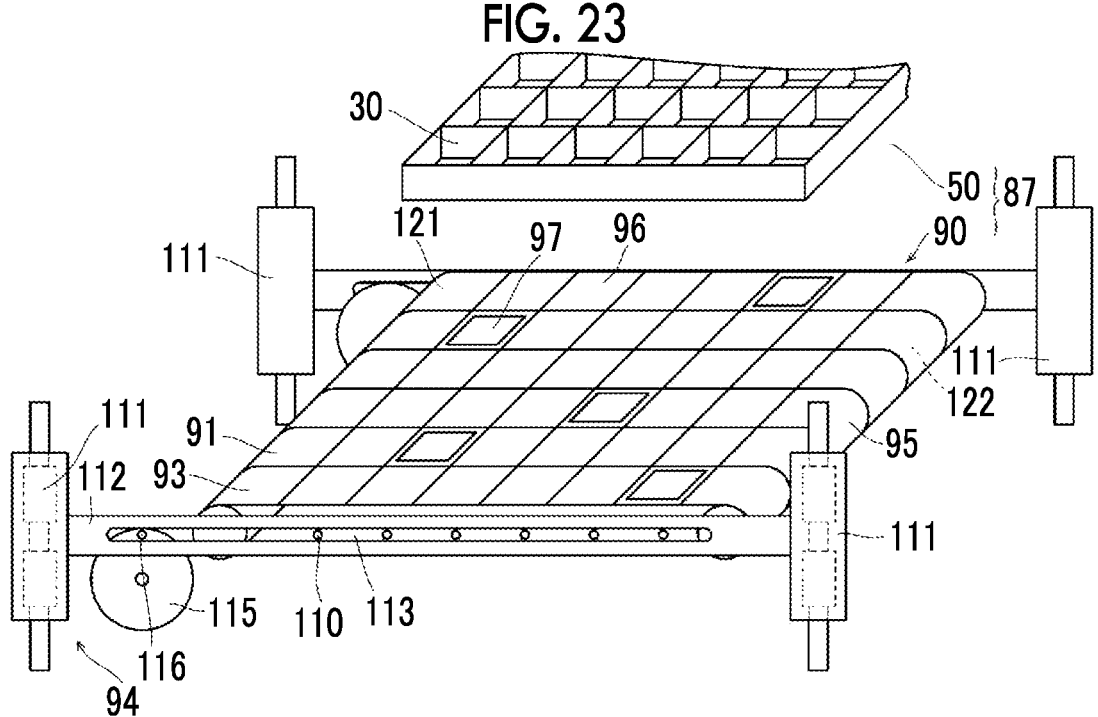
(a)
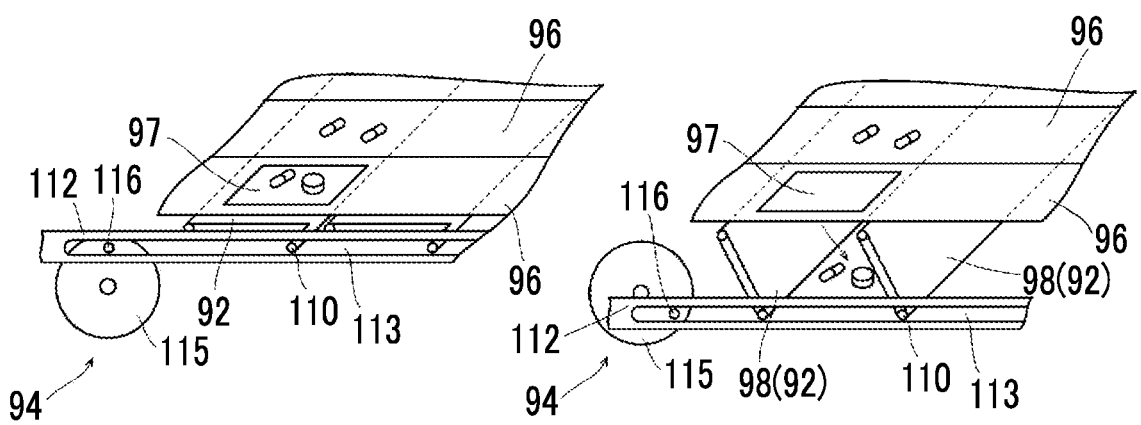
(b)
(c)

FIG. 24
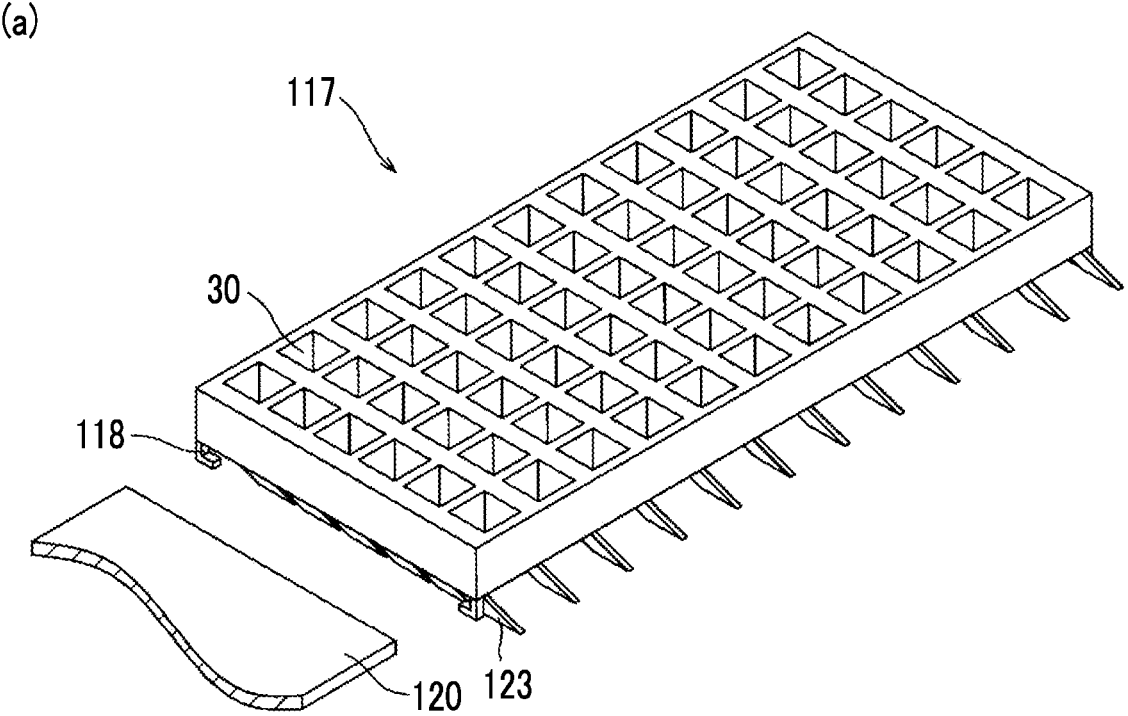
(a)
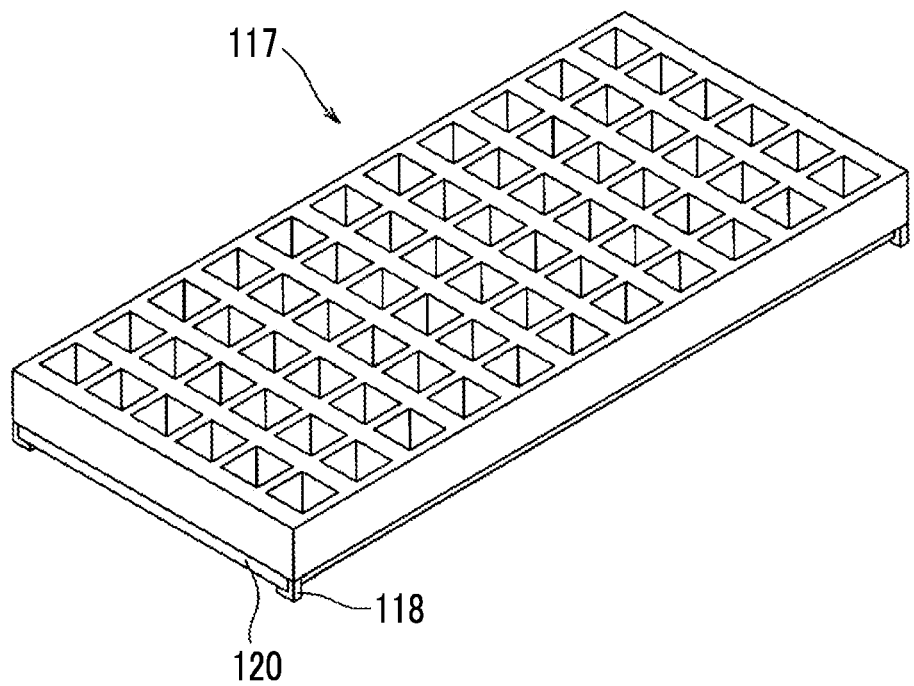
(b)

FIG. 25
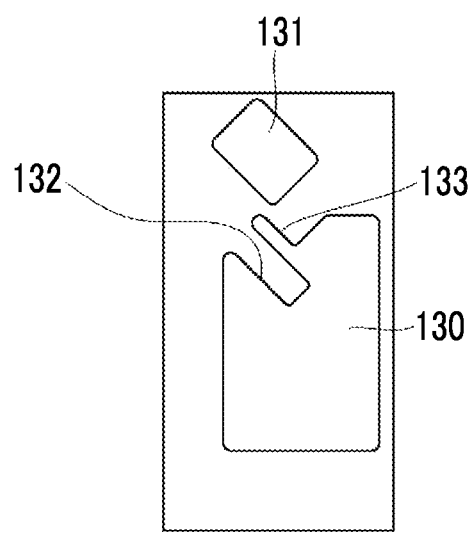
(a)
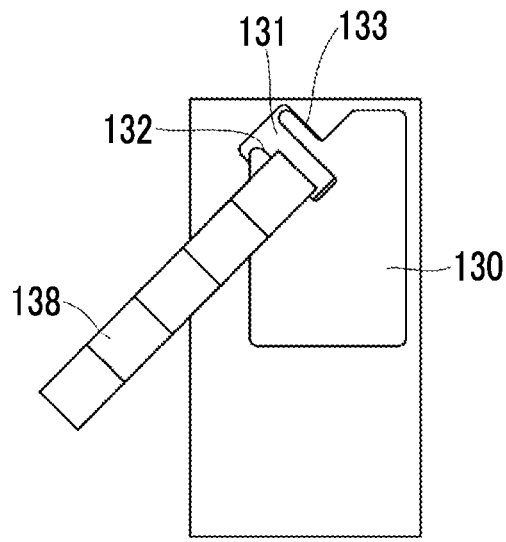
(b)
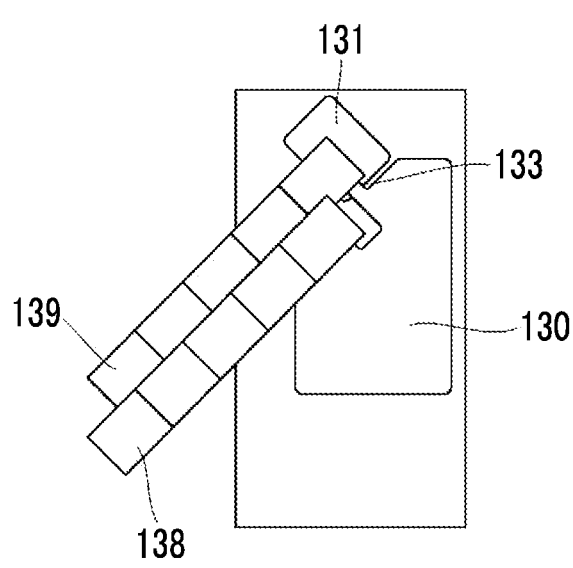
(c)
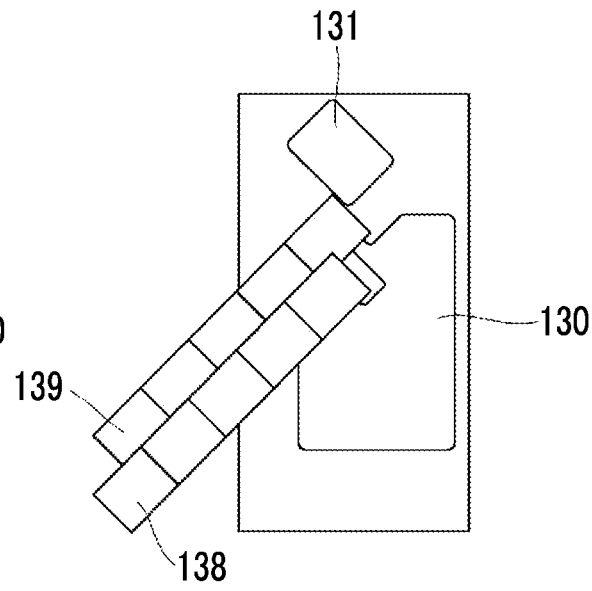
(d)

FIG. 27
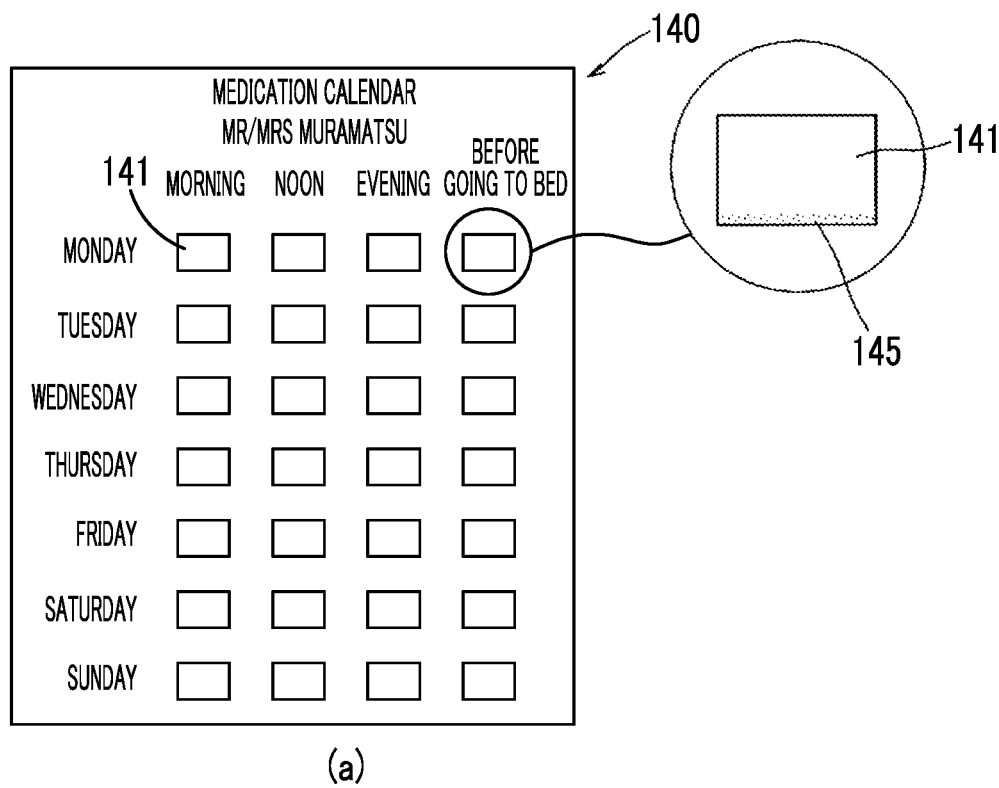
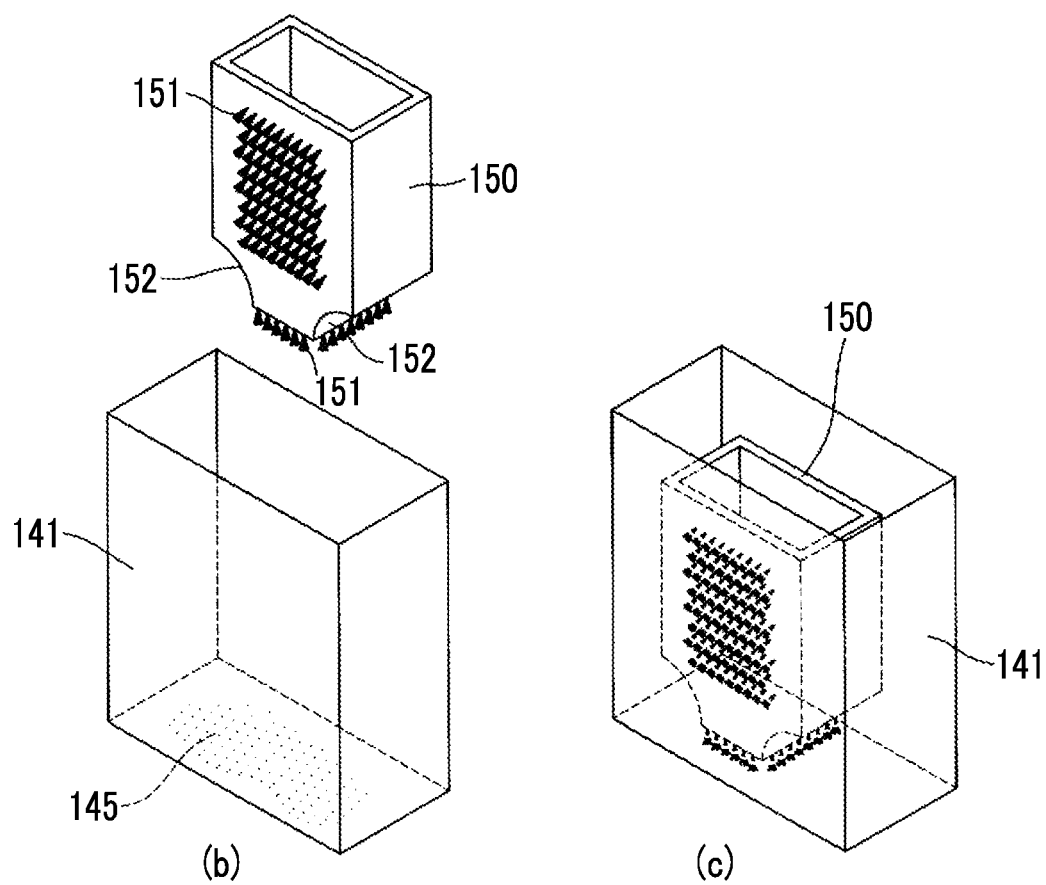

(a)
| NURSING HOME FOR ELDERLY FOR MORNING | MR/MRS a MORNING DRUG A | MR/MRS b MORNING DRUG B | MR/MRS c MORNING DRUG B |

(b)
| NURSING HOME FOR ELDERLY FOR NOON | MR/MRS a NOON DRUG D | MR/MRS b NOON DRUG F | MR/MRS c MORNING DRUG G |

(c)
| NURSING HOME FOR ELDERLY FOR EVENING | MR/MRS a EVENING DRUG B | MR/MRS b EVENING DRUG C | MR/MRS c EVENING DRUG A |

DRUG DISCHARGE DEVICE AND CONTROL METHOD FOR DRUG DISCHARGE DEVICE

RELATED APPLICATIONS

This application is the U.S. National Phase of and claims priority to International Patent Application No. PCT/JP2021/015095, International Filing Date Apr. 9, 2021; which claims benefit of Japanese Patent Application No. 2020-073984, filed Apr. 17, 2020; both of which are incorporated herein by reference in their entireties.

TECHNICAL FIELD

The present invention relates to a drug discharge device which is called a manual distribution device and discharges a solid drug to a packaging device or the like on the downstream side. In addition, the present invention also relates to a control method for a drug discharge device.

BACKGROUND ART

There is known a drug packaging device that packages a solid drug such as a tablet and a capsule one package one by one (Patent Literature 1). Normally, a drug packaging device includes a drug storage unit having a plurality of drug feeders and a drug packaging portion for packaging a drug. A drug cassette filled with a tablet or the like is attached to the drug feeder.

In the above-described drug packaging device, the drug feeder takes out the tablet stored in the drug cassette one by one, sends the tablet to the drug packaging portion, and packages the tablet for one dose one by one with packaging papers or the like.

In addition, a drug packaging device has a function called "manually distribution" among those skilled in the art, as disclosed in Patent Literature 2 below. Here, "manually distribution" refers to putting predetermined tablets one package one by one by fingers or a robot without using a drug feeder, and sending the tablets to the drug packaging portion to be packaged.

FIG. 28 is a perspective view of a manual distribution device adopted in a drug packaging device disclosed in Patent Literature 2.

A manual distribution device 100 disclosed in Patent Literature 2 includes a manual distribution member 102 and a divided blister unit 103. In the drug packaging device disclosed in Patent Literature 2, the divided blister unit 103 is disposed inside a main body (not illustrated). In addition, the manual distribution member 102 is attached so as to be manually slidable on a main body (not illustrated).

The manual distribution member 102 is a plate-like body in which recessed portions are provided in a vertical and horizontal matrix.

In addition, in the divided blister unit 103, blister portions are provided in a vertical and horizontal matrix. The arrangement of the blister portions of the divided blister unit 103 corresponds to the arrangement of the recessed portions of the manual distribution member 102.

The manual distribution member 102 is detachably attached to a drawer frame 101.

In the drug packaging device disclosed in Patent Literature 2, the manual distribution member 102 is pulled out from the main body together with the drawer frame 101.

A tablet is put into a recessed portion of the manual distribution member 102 with a finger.

Thereafter, the manual distribution member 102 is inserted into the main body (not illustrated) of the drug packaging device.

The manual distribution member 102 is located above the divided blister unit 103 when the manual distribution member 102 is in a state of being inserted into the main body. A bottom portion of each of the recessed portions of the manual distribution member 102 is opened, and the tablet in each of the recessed portions is put into the blister portion of the divided blister unit 103.

Thereafter, the bottom portions of the divided blister unit 103 are sequentially opened, and the tablets are sent by one package one by one to a drug packaging portion 105 provided at a lower portion and to be packaged.

CITATION LIST

Patent Literatures

PTL 1: JP-A-H2-269621
PTL 2: JP-A-2001-335002

SUMMARY OF INVENTION

Technical Problem

In the manual distribution device in the related art, the order of opening the blister portions of the divided blister unit 103 is fixed, and the blister portions of the divided blister unit 103 are opened one by one in order from the end portion.

For example, when a prescription of one patient (for example, patient a) is to take a drug A in the morning, to take a drug B at noon, and to take a drug C in the evening, a pharmacist puts the drug A for the morning in a recessed portion in the first row and first column of the manual distribution member 102, puts the drug B for the noon in a subsequent recessed portion in the first row and second column, and puts the drug C for the evening in a subsequent recessed portion in the first row and third column, and then repeat the operation.

From the manual distribution device, the drugs are discharged to the packaging unit on the downstream side in order of input, and are sequentially packaged for one dose one by one.

As a result, drug packages to be taken by patient a are discharged from the drug discharge device in the order of dosing timing such as morning, noon, and evening.

As described above, in the manual distribution device 100 in the related art, it was necessary to put the drugs into the recessed portions of the manual distribution member 102 in the order in which the drugs were required to be packaged, which required careful operation. Therefore, the mental burden on the pharmacist was heavy.

In addition, in recent years, when a pharmacy provides the drug to a nursing home and the like, there is a request from the nursing home for the pharmacy to sort out the drug packages for a plurality of patients according to dosing timing.

For example, when there are three patients accommodated in the facility, patient a, patient b, and patient c, a group for morning is formed by grouping together the drugs that the three patients take in the morning, a group for noon is formed by grouping together the drugs that the three patients take at noon, and a group for evening is formed by grouping together the drugs that the three patients take in the evening, which are carried into the nursing home.

For example, as illustrated in FIG. 29, a strip package in which the drug packages for patient a, patient b, and patient c each taken in the morning are continuous, a strip package in which the drug packages for patient a, patient b, and patient c, each taken at noon are continuous, and a strip package in which the drug packages for patient a, patient b, patient c each taken in the evening are continuous, are formed and carried into the nursing home.

Alternatively, the drugs are placed on a sheet called a medication calendar and carried into the nursing home.

Therefore, there is a request to perform the drug packages for a plurality of patients at once.

For example, drugs prescribed for patient a, patient b, and patient c are put into one manual distribution member 102 and discharged individually.

In this case, for example, the pharmacist was forced to perform a complicated operation such as putting the morning drug A for patient a into the recessed portion of the first row and first column of the manual distribution member 102, putting the morning drug B for patient b into the subsequent recessed portion in the first row and second column, putting the morning drug C for patient c into the subsequent recessed portion in the first row and third column, and putting the noon drug D for patient a into the subsequent recessed portion in the first row and fourth column, which was an extremely heavy burden on the pharmacist.

An object of the present invention is to provide a drug discharge device capable of reducing complexity when distributing a drug into a manual distribution device, paying attention to the above-described problems in the related art.

Solution to Problem

According to an aspect for solving the above-described problems, there is provided a drug discharge device including a manual distribution member that includes a plurality of recessed portions in which a solid drug is distributed, discharge means that discharges the drug distributed in the recessed portions to a downstream side directly or via another member, and a control device that controls the discharge means, in which the discharge means is capable of individually discharging a drug corresponding to a predetermined recessed portion, the control device assigns the same drug to the recessed portions in adjacent regions based on prescription information including information on a drug to be provided to a plurality of patients or one patient, and the discharge means discharges the drugs in a predetermined order.

As a rule of thumb, in a case where an individual takes a drug in a plurality of times, such as in the morning, at noon, in the evening, and before going to bed, a duplicate drug may be included in the drug to be taken.

In addition, drugs prescribed to a plurality of patients often contain the same drug. For example, patients accommodated in the nursing home for the elderly are often prescribed drugs that stabilize blood pressure or drugs that reduce natural fat, and these drugs are often the same as each other.

The present invention addresses this fact and assigns the same drug to the recessed portions in adjacent regions based on prescription information including information on a drug to be provided to the plurality of patients or one patient.

According to the present aspect, the same drug can be intensively distributed in a grouped region of the manual distribution member, so that the operation is simple and the burden on the pharmacist is reduced.

In addition, according to the present aspect, the discharge means can individually discharge the drug corresponding to the predetermined recessed portion, and discharge the drugs in a predetermined order to form a desired drug group. For example, a group for morning can be formed by grouping together the drugs that the three patients take in the morning, a group for noon can be formed by grouping together the drugs that the three patients take at noon, and a group for evening can be formed by grouping together the drugs that the three patients take in the evening.

In the above-described aspect, it is desirable that the recessed portion is distributed with one or a plurality of drugs for one dose, the drug for one dose is one type or a plurality of types of drugs, and the drug having the same type and number is assigned to the recessed portions in adjacent regions.

According to the present aspect, the drugs of the same number and type can be intensively distributed in a grouped region of the manual distribution member, so that the operation is simple and the burden on the pharmacist is reduced.

In the above-described aspect, it is desirable that the drug discharge device further includes display means, in which the display means is capable of displaying a simulated chart simulating an arrangement of the recessed portions, and information related to a drug required to be distributed is displayed on the simulated chart and/or the same screen as the simulated chart.

An operator such as a pharmacist can put the drug into a predetermined recessed portion while referring to the display device.

In the above-described aspect, it is desirable that a uniform mark is displayed on the recessed portion in which the same drug is required to be put in the simulated chart.

For example, coloring and a figure can be considered as the mark. For example, a configuration for color coding is considered for each region in which the same drug is put.

In each of the above-described aspects, it is desirable that the manual distribution member includes indicating means that indicates a recessed portion in which a drug is required to be put.

According to the present aspect, since the recessed portion in which the drug is required to be put is indicated, there are few mistakes in putting the drug.

In each of the above-described aspects, it is desirable that a divider is disposed below the manual distribution member, the divider includes a temporary accommodating member and a bottom constituting member, the temporary accommodating member includes a blister portion, and the blister portion corresponds to the recessed portion of the manual distribution member and a bottom side is opened, the bottom constituting member is capable of opening and closing a specific portion to form a drop opening, and the temporary accommodating member and the bottom constituting member are movable relative to each other, and at least one of the temporary accommodating member and the bottom constituting member is capable of being moved to move a specific blister portion to a position where the drop opening of the bottom constituting member is formed.

In the drug discharge device of the present aspect, the divider is disposed below the manual distribution member, and the temporary accommodating member of the divider includes the blister portion corresponding to the recessed portion of the manual distribution member.

In the drug discharge device of the present aspect, the drug distributed to the manual distribution member is once transferred to the lower divider, and then the blister portions of the divider are opened one by one to discharge the drug.

In the present aspect, as a measure for discharging the drug from the blister portion, a configuration is adopted in which the divider includes the temporary accommodating member that constitutes the blister portion, and the bottom constituting member.

In the drug discharge device of the present aspect, the bottom side of the blister portions is opened, but the bottom side of each of the blister portions is blocked by the bottom constituting member.

In addition, the bottom constituting member can open and close a specific portion to open the drop opening.

In the drug discharge device of the present aspect, the temporary accommodating member and the bottom constituting member are movable relative to each other, any one of the temporary accommodating member and the bottom constituting member is moved to move the specific blister portion to a position where the drop opening of the bottom constituting member can be formed, the bottom of the specific blister portion is opened, and the drug can be discharged from the specific blister portion.

In addition, an aspect is also conceivable in which a bottom side of the recessed portion of the manual distribution member is opened, and a bottom constituting member is provided below the manual distribution member, the bottom constituting member is capable of opening and closing a specific portion to form a drop opening, and the manual distribution member and the bottom constituting member are movable relative to each other, and at least one of the manual distribution member and the bottom constituting member is capable of being moved to move a specific recessed portion to a position where the drop opening of the bottom constituting member is formed.

In each of the above-described aspects, it is desirable that the bottom constituting member has an entire closed region and an openable region, the openable region is configured by arranging moving floor members having narrow flat surfaces, and the moving floor member is individually capable of moving in parallel, and the moving floor member is moved in parallel to form the drop opening between the entire closed region and the moving floor member.

A divider adopting the present aspect has a simple structure and a small overall shape.

According to another aspect for solving a similar problem, there is provided a drug discharge device including a manual distribution member that includes a plurality of recessed portions in which a solid drug is distributed, and discharge means that discharges the drug distributed in the recessed portions to a downstream side directly or via another member, in which the recessed portion is distributed with one or a plurality of drugs for one dose, and the drug discharge device further includes recessed portion determining means that determines a recessed portion required to be distributed based on a type of drug, and guidance means that guides a determined recessed portion.

Here, the "guidance means" includes the simulated chart simulating the arrangement of the recessed portions displayed on the display means, and the indicating means provided on the manual distribution member to indicate the recessed portions in which the drug is required to be put.

In the drug discharge device of the present aspect, the recessed portion in which the drug is required to be distributed is determined by the recessed portion determining means.

An operator such as a pharmacist can put the drug in a predetermined recessed portion while referring to the guidance means.

According to still another aspect for solving a similar problem, there is provided a drug discharge device including a plurality of drug feeders, a manual distribution member that includes a plurality of recessed portions in which a solid drug is distributed, and discharge means that discharges the drug distributed in the recessed portions to a downstream side directly or via another member, in which a drug cassette capable of being filled with a plurality of drugs is attached to the drug feeder, and the drug feeder discharges the drug from the drug cassette, the recessed portion is distributed with one or a plurality of drugs for one dose, and the drug discharge device further includes recessed portion determining means that distinguishes between a drug capable of being discharged from the drug feeder and a drug not capable of being discharged from the drug feeder, and determines a recessed portion required to be distributed based on a type of drug when discharging the drug not capable of being discharged via the manual distribution member.

The drug discharge device of the present aspect includes the plurality of drug feeders and the manual distribution member, and the drug is discharged mainly using the drug feeders. In the drug discharge device of the present aspect, the drug that cannot be discharged from the drug feeder is discharged via the manual distribution member, and at that time, the recessed portion required to be distributed is determined based on the type of drug.

A drug packaging device is configured to include any one of the drug discharge devices described above, and a packaging device that packages a drug discharged from the drug discharge device.

According to an aspect related to a method, there is provided a control method of a drug discharge device that includes a manual distribution member including a plurality of recessed portions in which a solid drug is distributed, and discharge means discharging the drug distributed in the recessed portions to a downstream side directly or via another member, the method including putting the same drug in the recessed portions in adjacent regions in a case where there is the same drug among the drugs supplied to a plurality of patients in response to prescriptions of the plurality of patients, and discharging the drug in order of dosing timing.

According to the control method of the drug discharge device of the present aspect, the same drug can be intensively distributed in a grouped region, so that a mental burden on the pharmacist is reduced.

Advantageous Effects of Invention

According to the drug discharge device of the present invention, the same drug can be intensively distributed in a grouped region, so that there is an effect of reducing complexity when distributing the drug into the manual distribution device.

In addition, according to the drug discharge device, there is an effect that it is easy to understand the recessed portion in which the drug is distributed, and it is possible to reduce mistakes.

BRIEF DESCRIPTION OF DRAWINGS

FIG. 4 is a display screen diagram illustrating an example of a display screen of a display device of the drug packaging device of FIG. 1, and illustrates an allocation status in a case of sorting drug packages for a plurality of patients by dosing timing and taking one tablet of solid drug at a time according to each dosing timing.

FIG. 5 is an explanatory diagram illustrating an outline of a patient's prescription.

FIG. 6 is a plan view of a manual distribution member, where (a) illustrates a preparation step, (b) is a plan view of the manual distribution member when a drug A is distributed, (c) is a plan view of the manual distribution member when a drug B is distributed, and (d) is an enlarged view of a recessed portion.

FIG. 8 is a perspective view of the manual distribution device of FIG. 7, and illustrating a view in which the manual distribution member and a divider are separated.

FIG. 9 (*a*) is an exploded perspective view of the divider of FIG. 7, and FIG. 9 (*b*) is a cross-sectional view of a temporary accommodating member.

FIG. 12 illustrates a step following FIG. 11 of the operation when discharging the drug from the blister portion of number 1 of the temporary accommodating member, where (a) is a plan view of the manual distribution device with the manual distribution member omitted at that time, and (b) is a cross-sectional view taken along the line A-A.

FIG. 13 illustrates a first step of an operation when discharging the drug from a blister portion of number 28 of the temporary accommodating member, where (a) is a plan view of the manual distribution device with the manual distribution member omitted at that time, and (b) is a cross-sectional view taken along the line A-A.

FIG. 14 illustrates a step following FIG. 13 of the operation when discharging the drug from the blister portion of number 28 of the temporary accommodating member, where (a) is a plan view of the manual distribution device with the manual distribution member omitted at that time, and (b) is a cross-sectional view taken along the line A-A.

FIG. 15 is a display screen diagram illustrating an example of the display screen of the display device of the drug packaging device of FIG. 1, and illustrates an allocation status in a case of sorting a drug package for one patient by dosing timing and taking one tablet of solid drug at a time according to each dosing timing.

FIG. 16 is a display screen diagram illustrating an example of the display screen of the display device of the drug packaging device of FIG. 1, and illustrates an allocation status in a case of sorting a drug package for one patient by dosing timing and taking a plurality of solid drugs according to each dosing timing.

FIG. 17 is a display screen diagram illustrating an example of the display screen of the display device of the drug packaging device of FIG. 1, and illustrates an allocation status in a case of sorting drug packages for a plurality of patients by dosing timing and taking a plurality of solid drugs according to each dosing timing.

FIG. 18 is a display screen diagram illustrating an example of the display screen of the display device of the drug packaging device of FIG. 1, and illustrates an allocation status in a case of sorting drug packages for one or a plurality of patients by dosing timing and taking a plurality of different types of drugs according to each dosing timing.

FIG. 19 is a display screen of an inspection device, where (a) illustrates a normal display, (b) illustrates a patient-by-patient display sorted by patient, and (c) illustrates a confirmation display that displays the front and rear of a specific location.

FIG. 20 illustrates a divider of a manual distribution member adopted in another embodiment of the present invention, where (a) is a plan view of an opening and closing mechanism portion, (b) is a perspective view of the opening and closing mechanism portion illustrating a state where a clutch is released, and (c) is a perspective view of the opening and closing mechanism portion illustrating a state where the clutch is engaged.

FIG. 21 illustrates the relationship between a blister portion of the temporary accommodating member of the divider and the opening and closing mechanism portion illustrated in FIG. 20, where (a) illustrates a state where a bottom of the blister portion is closed, and (b) illustrates the state where the bottom of the blister portion is open.

FIG. 22 illustrates a divider of a manual distribution member adopted in still another embodiment of the present invention, where (a) is a perspective view of an opening and closing mechanism portion, and (b), (c), and (d) are explanatory diagrams illustrating an operation of the opening and closing mechanism portion.

FIG. 23 illustrates a divider of a manual distribution member adopted in still another embodiment of the present invention, where (a) is an exploded perspective view thereof, and (b) and (c) are explanatory diagrams illustrating an operation of an opening and closing mechanism portion.

FIG. 24 is a temporary accommodating member of a divider of a manual distribution member adopted in still another embodiment of the present invention, where (a) illustrates a state before a closing plate is inserted into a main body portion, and (b) illustrates a state where the closing plate is inserted into the main body portion.

FIG. 25 is a front view illustrating a vicinity of a drug package discharge port of a drug discharge device, where (a) illustrates a state where a sorter is in a standby position, and (b), (c), and (d) illustrate a state where the sorter is operated.

FIG. 27 (*a*) is an enlarged view of a medication calendar and a drug accommodating portion, FIG. 27 (*b*) is a perspective view of a cleaning tool and the drug accommodating portion, illustrating a state before inserting the cleaning tool into the drug accommodating portion, and FIG. 27 (*c*) is a perspective view of the cleaning tool and the drug accommodating portion, illustrating a state when the cleaning tool is inserted into the drug accommodating portion for cleaning.

DESCRIPTION OF EMBODIMENTS

Embodiments of the present invention will be further described below.

Figure 1:
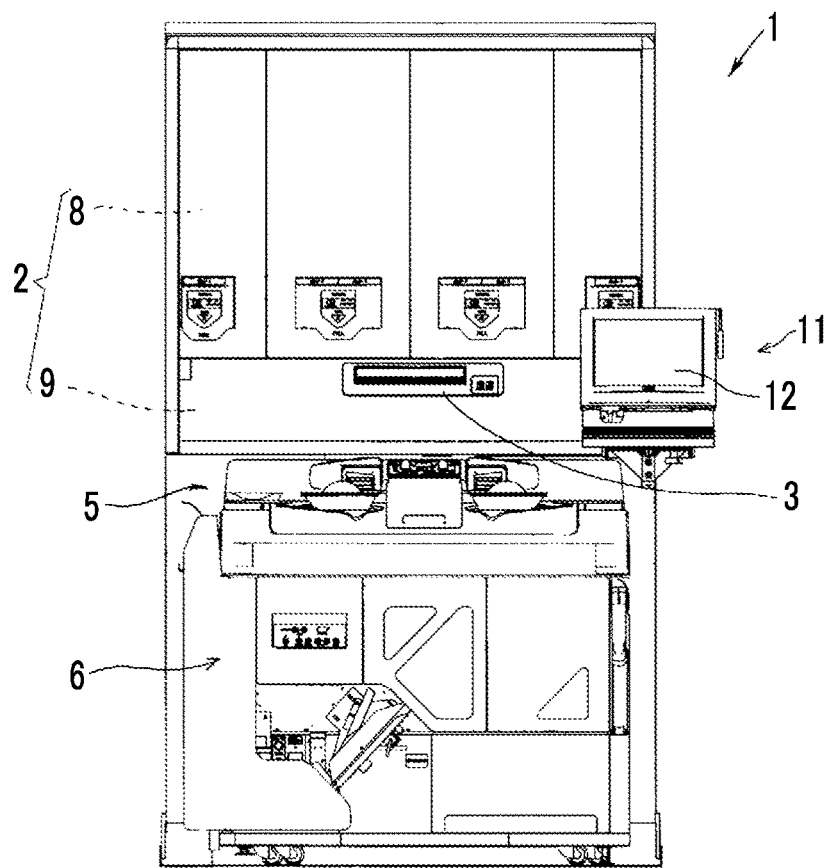
FIG. 1 is a front view of a drug packaging device according to an embodiment of the present invention.
Figure 2:
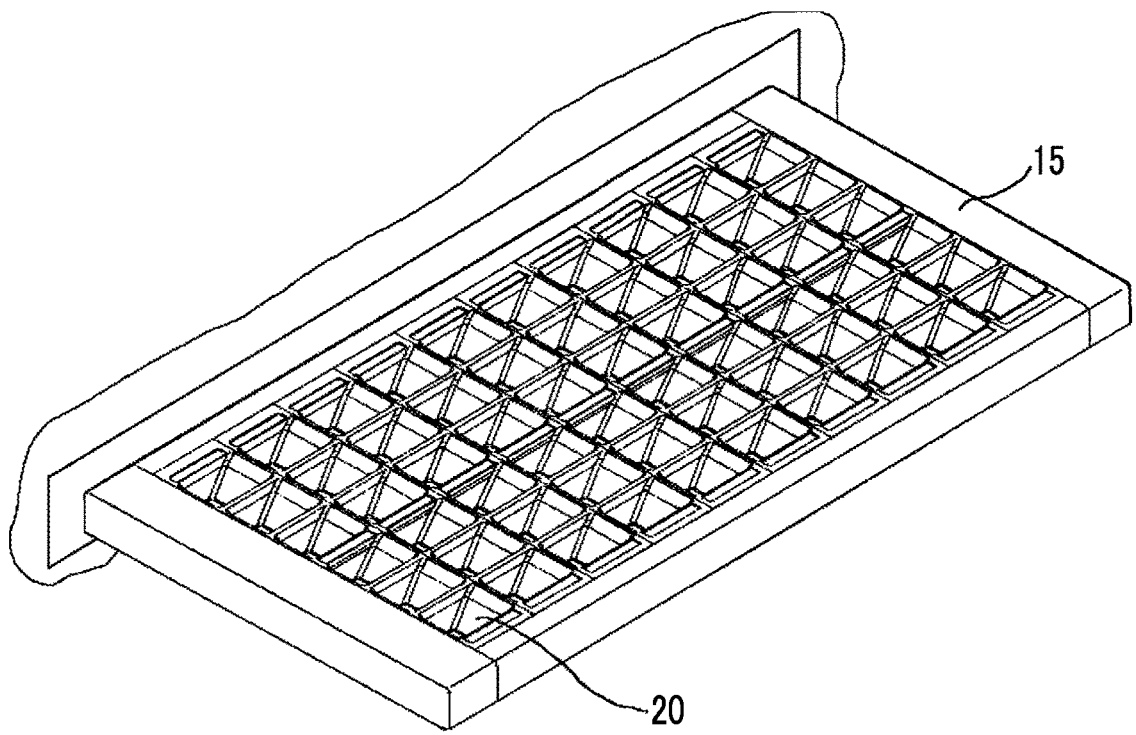
FIG. 2 is a perspective view of an insertion port of a main body portion and a manual distribution member in the drug packaging device of FIG. 1, as viewed obliquely from the front.

The drug packaging device 1 of the present embodiment has an external shape as illustrated in FIG. 1. The drug packaging device 1 is roughly divided into a tablet supply portion 2, a manual distribution portion 3, a powder supply portion 5, and a drug packaging portion 6. A manual distribution device (drug discharge device) 10 is built in the manual distribution portion 3.

Here, the tablet supply portion 2 occupies the upper half of the drug packaging device 1. The tablet supply portion 2 is configured to include a drug shelf portion 8 storing various types and large amount of tablets of solid drugs such as a capsule and a tablet (hereinafter, it may simply be referred to as a tablet), and a tablet transport path portion 9.

Multiple drug feeders (not illustrated) are built in the drug shelf portion 8. A drug cassette (not illustrated) is attached to each drug feeder.

Multiple tablets are stored in the drug cassette, and the tablets are discharged one by one from the drug cassette. The discharged tablets are sent to the drug packaging portion 6 and packaged in small bags for one dose one by one.

The powder supply portion 5 and the drug packaging portion 6 occupy the lower half of the drug packaging device 1, and both are built in this part.

The powdered drug scraped out from the powder supply portion 5 is also packaged in the same manner as tablets and the like.

The drug packaging device 1 is provided with a display device 11. The display device (guidance means) 11 is a known touch panel or the like, and includes a display screen 12.

Next, the outline of the manual distribution device 10, which is a characteristic part of the present embodiment, will be described.

Figure 7:
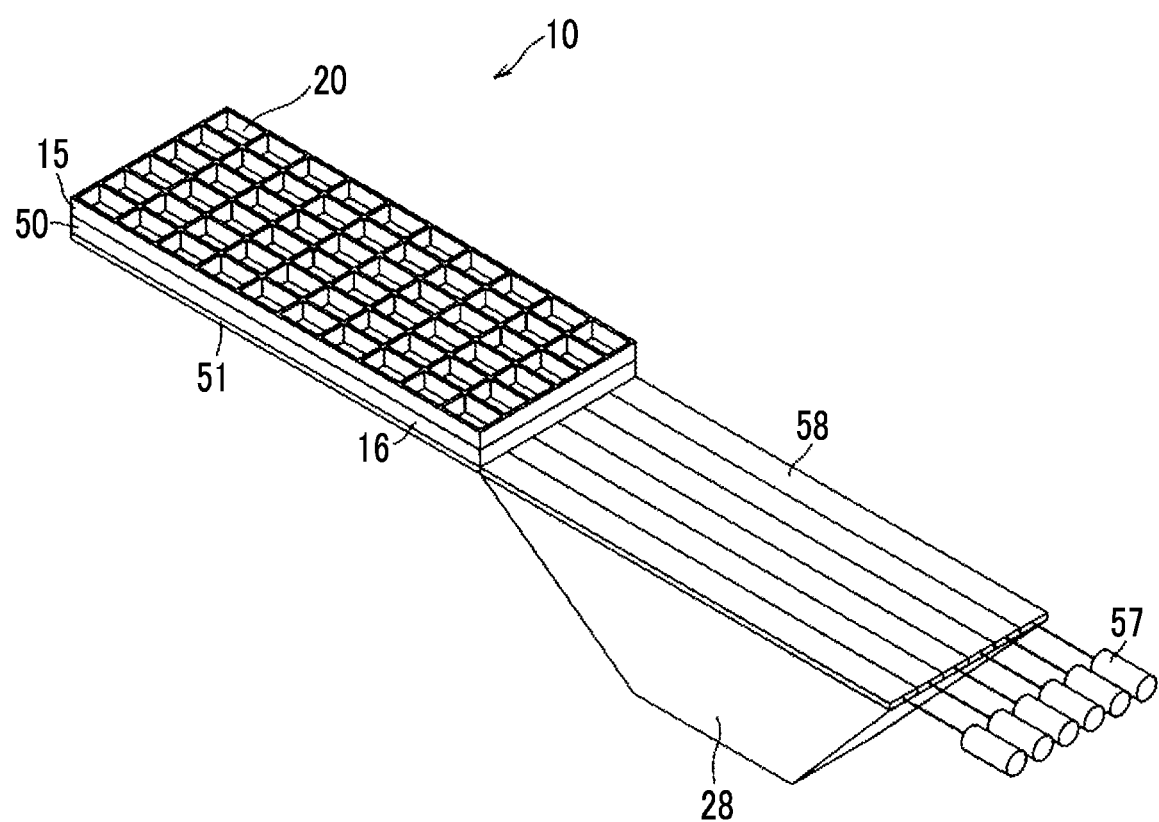
FIG. 7 is a perspective view of the manual distribution device (drug discharge device).
Figure 10:
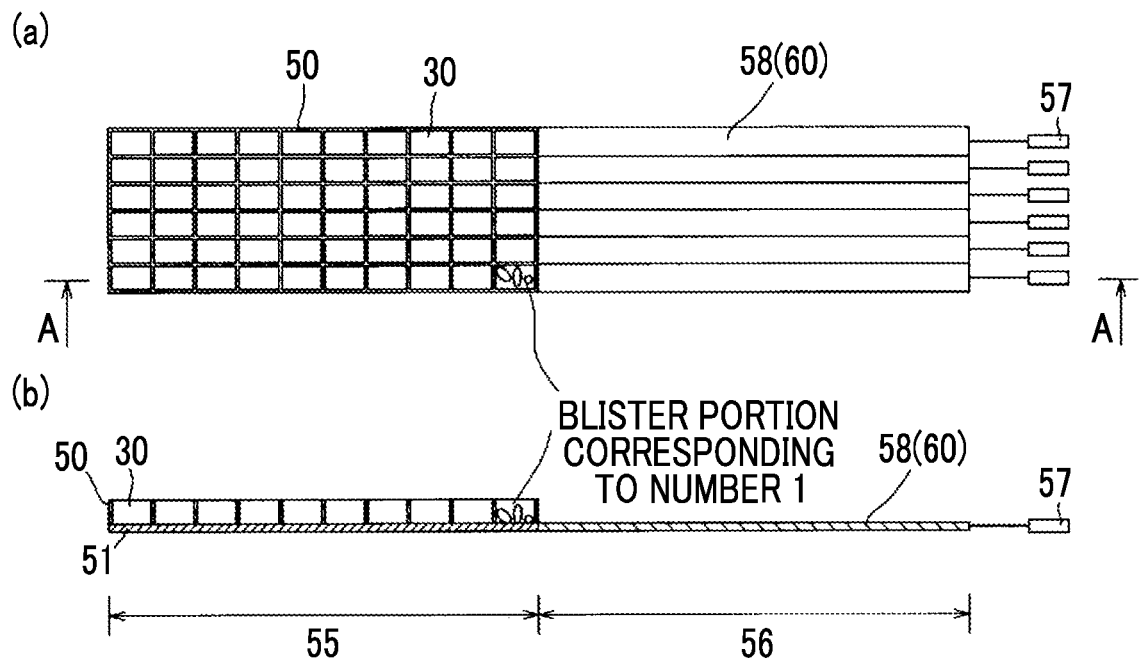
FIG. 10 (*a*) is a plan view of the manual distribution device with the manual distribution member omitted, and FIG. 10 (*b*) is a cross-sectional view taken along the line A-A.

The manual distribution device 10 is configured to include a manual distribution member 15 and a divider 16, as illustrated in FIG. 7.

The manual distribution member 15 is a member having a plate-like overall shape, and recessed portions 20 are arranged in a matrix. Each recessed portion 20 has a bottom (not illustrated). The bottom is openable and closable so that the bottom can be opened to transfer the drug in the recessed portion 20 to below the divider 16 as described later.

As illustrated in FIG. 6(d), each recessed portion 20 of the manual distribution member 15 is provided with an indicator lamp (indicating means or guidance means) 22, so that a specific recessed portion 20 can be illuminated and highlighted.

The divider 16 is a member provided with multiple blister portions 30 similar to the recessed portions 20 of the manual distribution member 15 described above. The layout, that is, the number and arrangement of the blister portions 30 provided in the divider 16 is the same as the layout of the recessed portions 20 of the manual distribution member 15 described above, and the blister portions 30 of the divider 16 are in one-to-one correspondence with the recessed portions 20 of the manual distribution member 15.

The divider 16 can open the blister portions 30 at predetermined positions in random order. The divider 16 is discharge means, and is capable of individually discharging a drug corresponding to a predetermined recessed portion.

As illustrated in FIG. 7, a collecting hopper 28 is provided below the divider (discharge means) 16. A terminal end of the collecting hopper 28 communicates with the passage leading to the drug packaging portion 6 described above.

The divider 16 of the manual distribution device (drug discharge device) 10 is accommodated in the main body portion of the drug packaging device 1. On the other hand, the manual distribution member 15 has a drawer-like structure and enters and exits from the main body portion of the drug packaging device 1.

When the manual distribution member 15 is accommodated in the main body portion of the drug packaging device 1, as illustrated in FIG. 7, the manual distribution member 15 reaches a position directly above the divider 16, and the bottom of the recessed portion 20 is completely opened so that the drug in the recessed portion 20 is transferred to the blister portion 30 of the divider 16.

Next, a control device 40 will be described.

Figure 3:
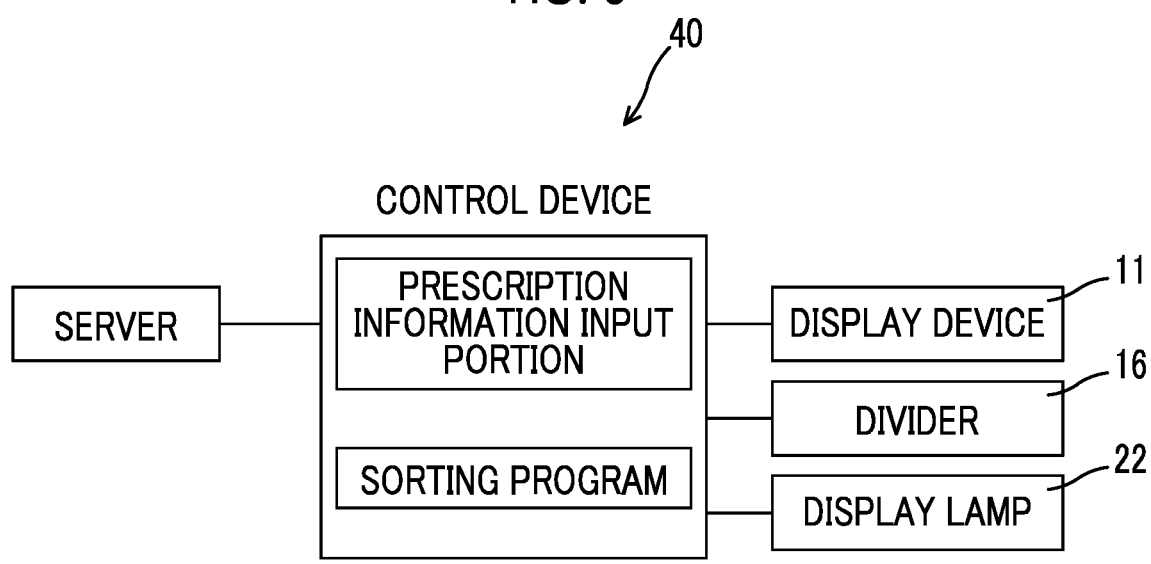
FIG. 3 is a block diagram of a control device that controls a manual distribution device (drug discharge device).

As illustrated in FIG. 3, the control device 40 performs control to assign the same drug to recessed portions in adjacent regions based on prescription information including information on drugs to be provided to a plurality of patients or one patient.

The control device 40 functions as recessed portion determining means for determining the recessed portion 20 to be distributed based on the type of drug.

In addition, the control device 40 also has a function of distinguishing between drugs that can be discharged from the drug feeder and drugs that cannot be discharged from the drug feeder.

These functions are realized by a sorting program.

The control device 40 has a known CPU, memory, and the like, and the sorting program is built in the memory. In addition, the control device 40 also has a prescription information input portion.

An external server is connected to the control device 40.

In the present embodiment, prescription information is input from the server. The prescription information includes information on the type and quantity of drug required. In addition, the prescription information also includes other information such as the quantity and dosing timing.

The display device 11, the divider 16, and the indicator lamp 22 of the manual distribution member 15 are connected to the output side of the control device.

The sorting program is a program that refers to the prescription information of a plurality of patients and that, in a case where there are common drugs, forms one group by grouping the common drugs.

Here, the prescription information includes the types of drugs, the amount of drugs, dosing timing, dosing method, and the like.

The sorting program selects drugs required to be distributed manually among the drugs included in the prescription information, and refers to the information on the drugs. Specifically, the types of drugs required to be distributed manually, the amount of dosing, the dosing timing, and the like are referred to.

That is, drugs included in prescription information include solid drugs, powdered drugs, ointments, and the like. In addition, solid drugs include those that are currently stored in the tablet supply portion 2 and can be discharged from the drug feeder, and those that are not stored in the tablet supply portion 2. The concept of prescription information also includes what is referred to as dispensing information processed for dispensing.

The sorting program is at least a program that refers to the information on solid drugs not currently stored in the tablet supply portion 2 and required to be discharged using the manual distribution device 10, and, that, in a case where there are common drugs, forms one group by grouping the common drugs.

The blister portions 30 in which the group of drugs is required to be accommodated are collectively assigned to one region. As described above, since the blister portions 30 of the divider 16 correspond to the recessed portions 20 of the manual distribution member 15 one-to-one, by assigning the drugs to the blister portions 30 of the divider 16, the recessed portion 20 (manual distribution member 15) into which each drug is substantially distributed is allocated.

That is, the sorting program is a program that determines the recessed portions 20 required to be distributed based on the type of drug.

As illustrated in FIG. 4, a simulated chart (guidance means) 18 simulating the manual distribution member 15 is displayed on the display screen 12 of the display device 11 to illustrate the assigned result.

For example, as illustrated in FIG. 4, each type of drug is displayed in different colors, and the drugs to be distributed in the region are displayed as A, B, and C, for example.

In addition, the indicator lamp (guidance means) 22 of the manual distribution member 15 is turned on to display the recessed portion 20 into which the specific drug is required to be distributed.

The drug packaging device 1 of the present embodiment can discharge necessary drugs based on prescription information input from the outside, and can package and discharge for one dose one by one.

Here, the drug packaging device 1 of the present embodiment has the following three types of patterns for packaging one dose one by one.

(1) Only the drugs discharged from the tablet supply portion 2 are packaged for one dose one by one.

(2) Only the drugs discharged by the manual distribution device 10 are packaged for one dose one by one.

(3) The drugs discharged from each of the tablet supply portion 2 and the manual distribution device 10 are combined and packaged for one dose one by one.

In addition, although there is a pattern in which the drug discharged from the powder supply portion 5 is packaged alone or together with tablets or the like, the handling of the drug discharged from the powder supply portion 5 is the same as that for the drug discharged from the tablet supply portion 2, so the description is omitted.

In the present embodiment, in a case where the prescription information includes a drug that is not stored in the tablet supply portion 2, the drug is sent from the manual distribution device 10 to the drug packaging portion 6 and packaged.

In the drug packaging device 1 of the present embodiment, drugs that can be discharged from the drug feeder are distinguished from drugs that cannot be discharged, and drugs that are not stored in the tablet supply portion 2 and cannot be discharged from the drug feeder are discharged from the manual distribution device 10.

An operator such as a pharmacist refers to the simulated chart 18 displayed on the display device 11 and the indicator lamp 22 of the manual distribution member 15 to put a specific drug into the recessed portion 20 belonging to a predetermined region of the manual distribution member 15.

When it is time to discharge the specific drug, one of the blister portions 30 belonging to the region where the drug is grouped is opened, and the drugs are discharged from the opened blister portion 30.

Hereinafter, as illustrated in the table of FIG. 5, the case of creating drug packages for patients a to j will be described as an example. In addition, for convenience of description, as illustrated in FIG. 4, the recessed portions 20 of the manual distribution member 15 are numbered from the end.

According to the example, patients a to j are each provided with the drug four times: in the morning, at noon, in the evening, and before going to bed. Here, a blank column indicates when a drug that can be supplied from the tablet supply portion 2 is taken, and the drug corresponding to the blank column is automatically supplied from the tablet supply portion 2.

In addition, in many cases, the drugs are supplied from both the tablet supply portion 2 and the like and the manual distribution member 15 and are packaged together in one drug package.

For example, in a case where patient a takes a drug (not illustrated) in the morning, in addition to the drug A illustrated in the table of FIG. 5, and the drug is stored in the tablet supply portion 2, drugs supplied from both the tablet supply portion 2 and the manual distribution member 15, and both drugs are sent to the drug packaging portion 6 at the same time and packaged.

According to the example, drugs A are prescribed for patients a, c, f, g, and i. Drugs B are prescribed for patients b, d, g, and i. Drugs C are prescribed for patients e and h. Drug D is prescribed to patient j.

Supposing that drug packages for five days are required, 25 packages of drug A are required, 20 packages of drug B are required, ten packages of drug C are required, and five packages of drug D are required.

For example, in a case where the number of drugs A to be distributed in the recessed portions 20 is the same for each patient or each dosing timing, and supposing that all the drug A prescribed for each patient or each dosing timing are one tablet, one tablet of the drug A is assigned to each of regions from numbers 1 to 25 of the recessed portions 20 at a time. Other drugs B to D are also assigned in the same manner. Specifically, in a case where all the drugs B to D to be distributed in the recessed portion 20 for each patient or each dosing timing are one tablet, one tablet of the drug B is assigned to each of regions from numbers 26 to 45 of the recessed portions 20 at a time, one tablet of drug C is assigned to each of regions from numbers 46 to 55 of the recessed portions 20 at a time, and one tablet of drug D is assigned to each of regions from numbers 56 to 60 of the recessed portions 20 at a time.

In a case where the prescription information as described above is input to the control device 40, the regions from numbers 1 to 25 of the recessed portions 20 are defined as a region for the drug A. In addition, the regions from numbers 26 to 45 of the recessed portions 20 are defined as a region for the drug B. Similarly, allocation is performed so that the regions from numbers 46 to 55 of the recessed portions 20 are defined as a region for the drug C, and the regions from numbers 56 to 60 of the recessed portions 20 are defined as a region for the drug D.

As illustrated in FIG. 4, the simulated chart 18 is displayed on the display screen 12 of the display device 11 to illustrate the allocated result. The simulated chart 18 is color-coded by region into which the drug is put. In addition, the types of drugs are displayed in a frame corresponding to the recessed portion 20. In this manner, a uniform mark is displayed on the frame of the recessed portion 20 into which the same drug is required to be put in the simulated chart 18.

As described above, the operator such as a pharmacist refers to the simulated chart 18 displayed on the display device 11 and the indicator lamp 22 of the manual distribution member 15 to put a specific drug into the recessed portion 20 belonging to a predetermined region of the manual distribution member 15.

In a case where the number of drugs to be distributed in the recessed portion 20 is not the same for each patient or for each dosing timing, drugs A are assigned to the recessed portions 20 of numbers 1 to 25 by grouping the same number of drugs or by grouping drugs in the order of the patient. Other drugs B to D are similarly assigned.

In the present embodiment, as illustrated in FIG. 6(b), the indicator lamp 22 of the region for the drug A of the manual distribution member 15 is first turned on. When the distribution of the drug A into the region for the drug A is ended, an end switch (not illustrated) is pressed.

As a result, the lighting region of the manual distribution member 15 changes, and the indicator lamp of the region for the drug B of the manual distribution member 15 is turned on as illustrated in FIG. 6(c). Hereinafter, similarly, the lighting region of the manual distribution member 15 changes.

Instead of the end switch, a camera, sensor, or weight may be used to automatically detect the end of distribution and change the lighting region.

When the distribution of the drug to the manual distribution member 15 is ended, a predetermined end switch is pressed. As a result, the manual distribution member 15 is accommodated in the main body portion of the drug packaging device 1, and the manual distribution member 15 reaches a position directly above the divider 16, and the bottom of the recessed portion 20 is completely opened so that the drug in the recessed portion 20 is transferred to the blister portion 30 of the divider 16. A structure in which the manual distribution member 15 is manually pushed into the main body portion and accommodated may be adopted.

When the manual distribution operation is ended and the time comes to discharge the drug from the manual distribution device (drug discharge device) 10, any one of the blister portions 30 of the divider 16 corresponding to the region where the drugs are grouped is opened and the drug is discharged.

For example, when it is the turn to package the morning drug for patient a, the blister portion 30 corresponding to one of the regions for the drug A from numbers 1 to 25 of the recessed portion 20 is opened and the drug A is discharged. For example, when it is the turn to package the noon drug for patient h, the blister portion 30 corresponding to one of the regions for the drug C from numbers 46 to 55 of the recessed portion 20 is opened and the drug C is discharged.

According to the manual distribution device of the present embodiment, the drugs can be discharged in a predetermined order, and sorting suitable for delivering the drugs to the above nursing home can be performed.

That is, a group for morning can be formed by grouping together the drugs that each patient takes in the morning, a group for noon can be formed by grouping together the drugs that each patient takes at noon, a group for evening can be formed by grouping together the drugs that each patient takes in the evening, and a group for before going to bed can be formed by grouping together the drugs that each patient takes before going to bed, which can be carried into a nursing home or the like. In addition, if necessary, the drug package is set in the medication calendar and carried into a nursing home or the like.

For example, in a case where a group for morning is formed by grouping together the drugs that each patient takes in the morning, the procedure is as follows.

According to the table of FIG. 5, the drugs taken in the morning are the drug A for patient a, the drugs discharged from the tablet supply portion 2 for patient b and patient c, the drug B for patient d, the drug C for patient e, the drug A for patient f, the drug B for patient g, the drugs discharged from the tablet supply portion 2 for patient h, the drug A for patient i, and the drug discharged from the tablet supply portion 2 for patient j.

In a case where a group for morning is formed by grouping together the drugs that each patient takes in the morning, the drugs are discharged in the order described above.

Specifically, first, the blister portion 30 corresponding to the recessed portion 20 of number 1 belonging to the region for the drug A is opened, and the drug A for patient a is discharged. Subsequently, the drug for patient b and the drug for patient c are sequentially discharged from the tablet supply portion 2. Subsequently, the blister portion 30 corresponding to the recessed portion 20 of number 26 belonging to the region for the drug B is opened, and the drug B for patient d is discharged. Subsequently, the blister portion 30 corresponding to the recessed portion 20 of number 46 belonging to the region for the drug C is opened, and the drug C for patient e is discharged. Subsequently, the blister portion 30 corresponding to the recessed portion 20 of number 2 belonging to the region for the drug A is opened, and the drug A for patient f is discharged. Subsequently, the blister portion 30 corresponding to the recessed portion 20 of number 27 belonging to the region for the drug B is opened, and the drug B for patient g is discharged. Subsequently, the drug for patient h is discharged from the tablet supply portion 2. Subsequently, the blister portion 30 corresponding to the recessed portion 20 of number 3 belonging to the region for the drug A is opened, and the drug A for patient i is discharged. Subsequently, the drug for patient j is discharged from the tablet supply portion 2.

In this manner, the drugs that each patient takes in the morning can be sequentially discharged to form a group for morning.

Next, the recommended structure of the divider 16 will be described.

The manual distribution device 10 of the present embodiment includes the manual distribution member 15 and the divider 16 as illustrated in FIG. 7.

In addition, the divider 16 includes a temporary accommodating member 50 and a bottom constituting member 51, as illustrated in FIGS. 8 and 9(a).

The temporary accommodating member 50 includes a plurality of blister portions 30, and the arrangement of the blister portions 30 corresponds to that of the recessed portions 20 of the manual distribution member 15 one-to-one.

As illustrated in FIG. 9(b), the blister portion 30 of the temporary accommodating member 50 has no bottom, and the blister portion 30 itself is normally opened. However, there is the bottom constituting member 51 on the bottom side of the temporary accommodating member 50, and the bottom side of the blister portion 30 is closed by the bottom constituting member 51.

The bottom constituting member 51 is configured to include an entire closed region 55 and an openable region 56.

The entire closed region 55 is configured to include a single plate and has substantially no openings.

On the other hand, the openable region 56 is configured by arranging six moving floor members 58 in a plane. The moving floor member 58 includes a narrow planar strip-shaped member 60.

The moving floor member 58 can be individually moved in parallel by one blister by a driving source 57 such as a solenoid. As a result, a drop opening 61 is formed at a boundary portion between the entire closed region 55 and the openable region 56.

The entire closed region 55 described above has an area only to cover the entire bottom of the temporary accommodating member 50.

Similarly, the openable region 56 has an area only to cover the entire bottom of the temporary accommodating member 50 in a state where the six strip-shaped members 60 are combined in a rectangular shape.

In addition, in the divider 16 adopted in the present embodiment, the temporary accommodating member 50 is moved in parallel by a driving source (not illustrated), and can be stopped at a predetermined position.

In the manual distribution device 10 of the present embodiment as well, when the manual distribution member 15 is accommodated in the main body portion of the drug packaging device 1, the manual distribution member 15 reaches a position directly above the divider 16, and the bottom of the recessed portion 20 is completely opened so that the drug in the recessed portion 20 is transferred to the blister portion 30 of the temporary accommodating member 50.

The manual distribution device (drug discharge device) 10 of the present embodiment includes discharge means for temporarily opening the bottom of the blister portion 30 at a predetermined position to discharge the drug from the blister portion 30. The discharge means is configured to include the temporary accommodating member 50 described above and the bottom constituting member 51.

The discharge procedure will be described below.

Figure 11:
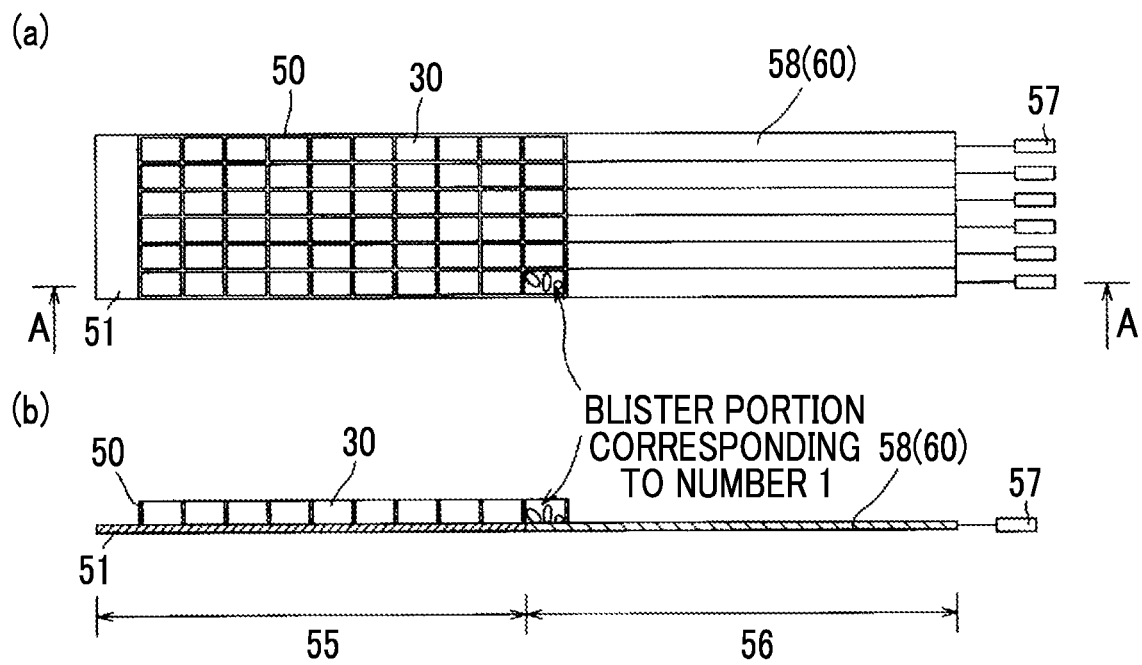
FIG. 11 illustrates a first step of an operation when discharging the drug from a blister portion of the number 1 of the temporary accommodating member, where (a) is a plan view of the manual distribution device with the manual distribution member omitted at that time, and (b) is a cross-sectional view taken along the line A-A.

For example, in a case of opening the blister portion 30 corresponding to the recessed portion 20 of number 1, the temporary accommodating member 50 is moved by one blister as illustrated in FIG. 11. Subsequently, as illustrated in FIG. 12, the moving floor member 58 in the first column is moved by one blister to form a drop opening 61 for one blister between the entire closed region 55 and the openable region 56. As a result, the bottom of the blister portion 30 corresponding to the recessed portion of number 1 is released, and the drug 62 is released from the recessed portion of number 1.

Next, the case of releasing the blister portion 30 corresponding to the recessed portion 20 of the central number 28 will be described. The blister portion 30 corresponding to number 28 is in the fifth row from the right and in the fourth column from the bottom.

In a case where the blister portion 30 corresponding to number 28 is released, the temporary accommodating member 50 is moved only by five blisters as illustrated in FIG. 13.

At this time, the temporary accommodating member 50 protrudes significantly from the entire closed region 55, but the openable region 56 has an area only to cover the entire bottom portion of the temporary accommodating member 50, so that the bottom of each blister portion 30 is maintained closed.

Subsequently, as illustrated in FIG. 14, the moving floor member 58 in the fourth column from the bottom is moved by one blister, and the drop opening 61 for one blister is formed in the portion of the fourth column between the entire closed region 55 and the openable region 56. As a result, the bottom of the blister portion 30 corresponding to the recessed portion 20 of number 28 is released, and the drug 62 is released from the recessed portion 20 of number 28.

In the embodiment described above, a plurality of moving floor members 58 are provided and each moving floor member 58 is moved independently to form only one drop opening 61, but an opening and closing member may be provided at a specific position, and the opening and closing member may be opened and closed by a motor or a solenoid.

For example, six openings may be formed side by side in the column direction at the boundary portion between the entire closed region 55 and the openable region 56, each opening may be provided with an opening and closing member such as a hinge that can be opened and closed, and the hinge or the like may be opened and closed by a motor or a solenoid.

The number of drugs put into each recessed portion 20 of the manual distribution member 15 is random, and may be one or a plurality of drugs.

In a case where the patient needs to take a plurality of drugs of the same drug at the same time, the plurality of drugs may be supplied to the drug packaging portion 6 by performing the operation of putting drugs one by one into the recessed portion 20 and discharging the drug from the blister portion 30, a plurality of times.

Drugs may be transferred from the recessed portions 20 accommodating different drugs to a plurality of blister portions 30, and the drugs may be supplied from the plurality of blister portions 30 to one drug package.

In addition, it does not deny that the drug for one dose is divided into a plurality of drug packages and accommodated.

The manual distribution device (drug discharge device) 10 of the embodiment described above discharges the drug distributed into the recessed portion 20 of the manual distribution member 15 via the divider 16, and the drug may be discharged directly from the manual distribution member 15 by individually opening and closing the recessed portions 20 of the manual distribution member 15.

For example, the recessed portion 20 of the manual distribution member 15 has a structure having no bottom and an open bottom portion. The bottom constituting member 51 as described above is disposed below the manual distribution member 15, the manual distribution member 15 and the bottom constituting member 51 can be moved relative to each other, at least one of the manual distribution member 15 and the bottom constituting member 51 is moved to move the specific recessed portion 20 to a position where the drop opening 61 of the bottom constituting member 51 is formed.

In the embodiment described above, the operation of sorting the drug packages for a plurality of patients according to dosing timing using the manual distribution device 10 has been described. The usage aspect described above is an example in a case where the drug to be distributed into the recessed portion 20 of the manual distribution member 15 is one tablet at a time.

Figure 19:
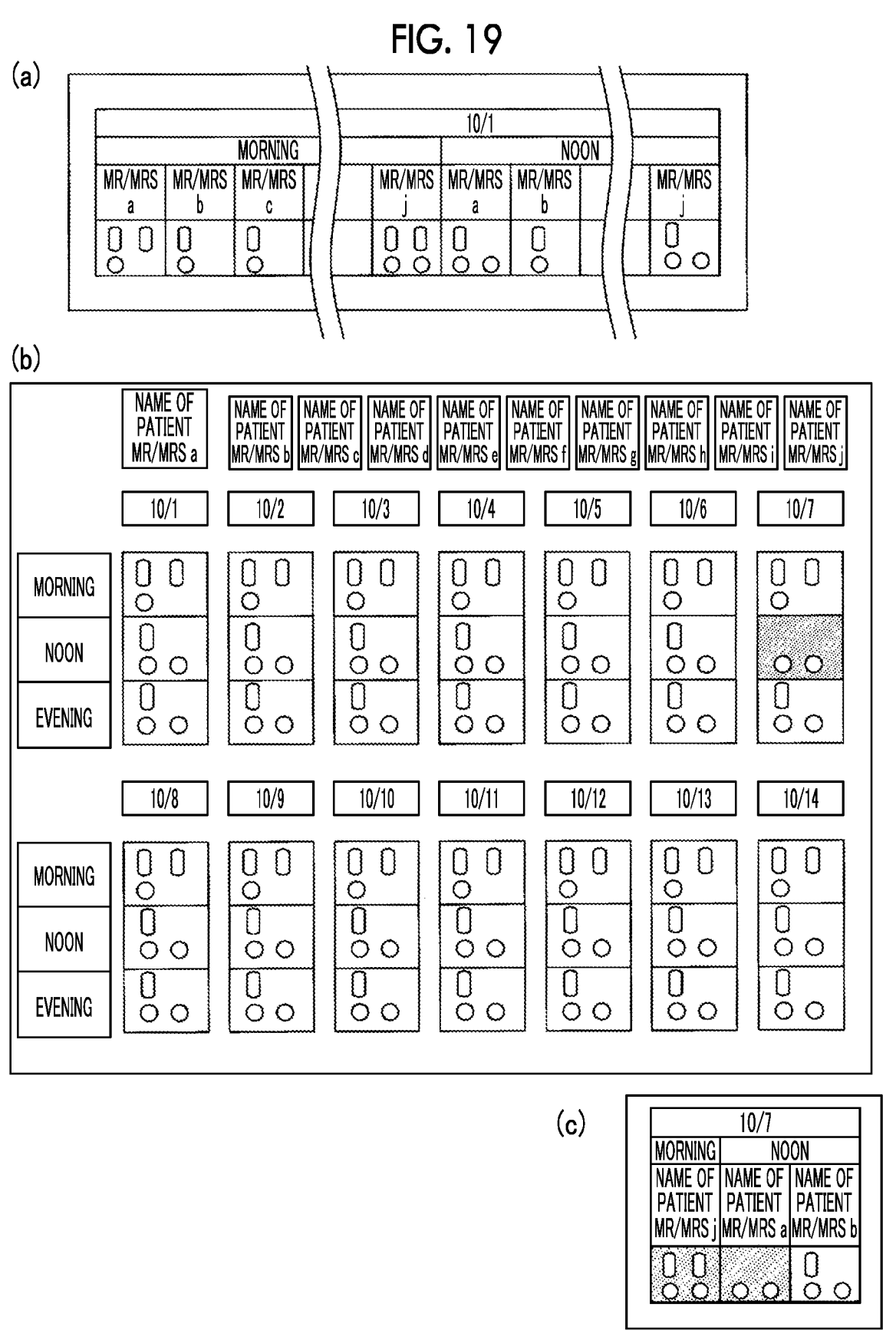

According to the usage aspect described above, it is possible to prepare a strip package in which drug packages to be taken at the same time are continuous, as illustrated in FIG. 19.

Other usage aspects include the following usage examples. In any case, one recessed portion 20 is distributed with the drug to be supplied from the manual distribution device (drug discharge device) 10 and to be taken at one time. In addition, in either case, the drugs of the same type and number are assigned to the recessed portions in the adjacent regions.

(1) A case where drug packages for one patient are sorted according to dosing timing, and one tablet of solid drug at a time may be taken at each dosing timing.

(2) A case where drug packages for one patient are sorted according to dosing timing, and a plurality of solid drugs may be taken at each dosing timing.

(3) A case where drug packages for a plurality of patients are sorted according to dosing timing, and a plurality of solid drugs may be taken at each dosing timing.

(4) A case where drug packages for one or a plurality of patients are sorted according to dosing timing, and a plurality of types of drugs may be taken at each dosing timing.

This will be described below.

(1) A case where drug packages for one patient are sorted according to dosing timing, and one tablet of solid drug at a time may be taken at each dosing timing.

For example, patient a takes the drugs A in the morning and in the evening, and takes the drug B at noon.

Supposing that drug packages for four days are prepared, eight packages of drug A are required and four packages of drug B are required.

Figure 15:
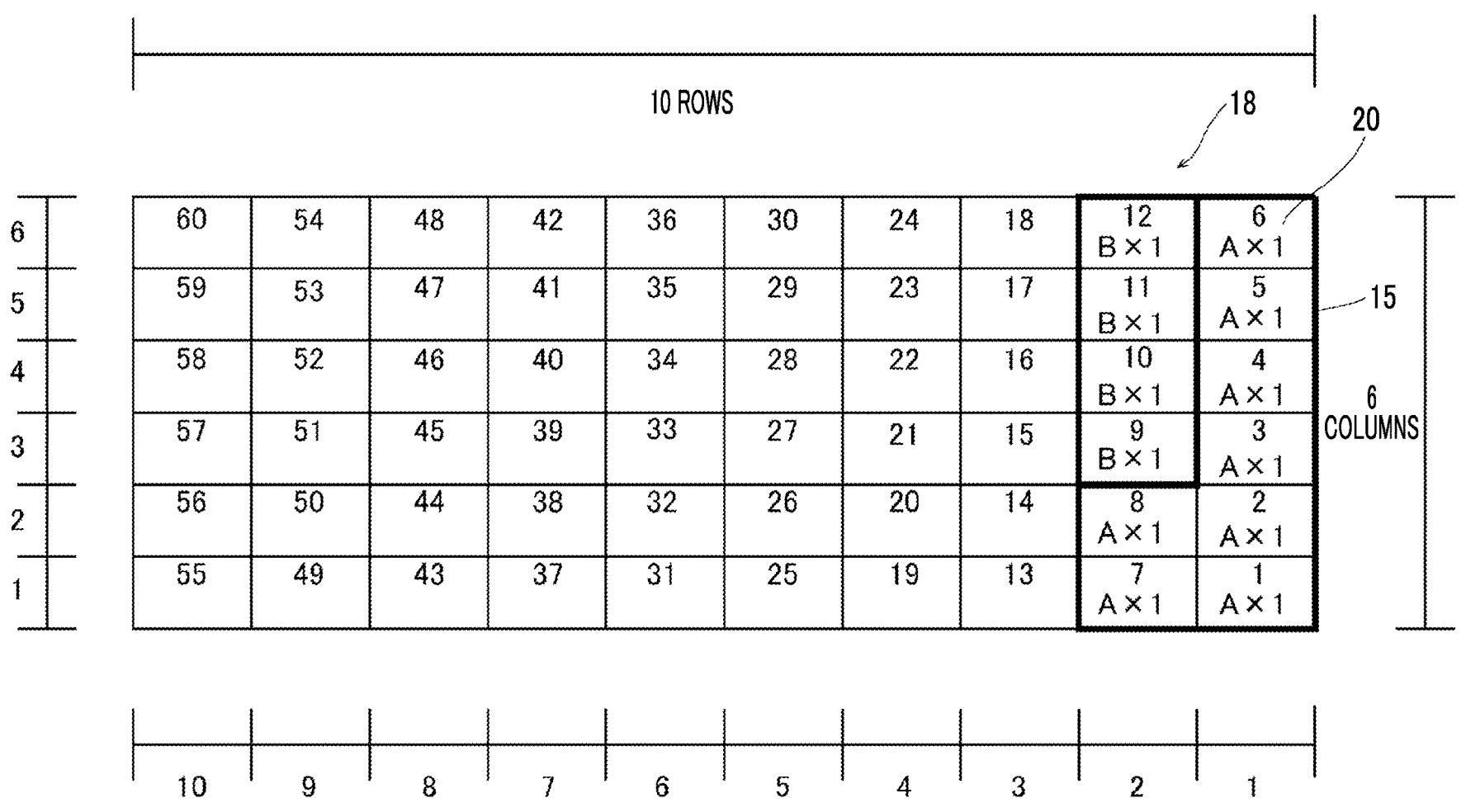

In this case, as illustrated in FIG. 15, one tablet of the drug A is assigned to the recessed portions 20 from numbers 1 to 8 at a time. One tablet of drug B is assigned to the subsequent recessed portions 20 from numbers 9 to 12 at a time.

(2) A case where drug packages for one patient are sorted according to dosing timing, and a plurality of solid drugs may be taken at each dosing timing.

For example, patient a takes one tablet of drug A in the morning, one tablet of drug B at noon, and two tablets of drug A in the evening.

Supposing that drug packages for four days are prepared, four drug packages in which one tablet of drug A is packaged are required, four drug packages in which two tablets of drug A are packaged are required, and four drug packages in which one tablet of drug B is packaged are required.

In this case, as illustrated in FIG. 16, the recessed portions 20 from numbers 1 to 4 are assigned as regions into which one tablet of the drug A is put at a time. The subsequent recessed portions 20 from numbers 5 to 8 are assigned as regions into which two tablets of drug A are put at a time. The subsequent recessed portions 20 from numbers 9 to 12 are assigned as regions into which one tablet of the drug B is put at a time.

(3) A case where drug packages for a plurality of patients are sorted according to dosing timing, and a plurality of solid drugs may be taken at each dosing timing.

For example, patient a takes one tablet of drug A in the morning, one tablet of drug B at noon, and two tablets of drug A in the evening. For example, patient b takes one tablet of drug A in the morning, one tablet of drug B at noon, and two tablets of drug A in the evening.

Supposing that drug packages for four days are prepared, eight drug packages in which one tablet of drug A is packaged are required, eight drug packages in which two tablets of drug A are packaged are required, and eight drug packages in which one tablet of drug B is packaged are required.

In this case, as illustrated in FIG. 17, the recessed portions 20 from numbers 1 to 8 are assigned as regions into which one tablet of the drug A is put at a time. The subsequent recessed portions 20 from numbers 9 to 16 are assigned as regions into which two tablets of drug A are put at a time. The subsequent recessed portions 20 from numbers 17 to 24 are assigned as regions into which one tablet of the drug B is put at a time.

(4) A case where drug packages for one or a plurality of patients are sorted according to dosing timing, and a plurality of types of drugs may be taken at each dosing timing.

For example, patient a takes one tablet of drug A and one tablet of drug B in the morning, one tablet of drug B at noon, and two tablets of drug A in the evening. For example, patient b takes two tablets of drug A in the morning, one tablet of drug B at noon, and one tablet of drug A and one tablet of drug B in the evening.

Supposing that drug packages for four days are prepared, eight drug packages in which one tablet of drug A and one tablet of drug B are packaged in one bag are required, eight drug packages in which two tablets of drug A are packaged are required, and eight drug packages in which one tablet of drug B is packaged are required.

In this case, as illustrated in FIG. 18, the recessed portions 20 from numbers 1 to 8 are assigned as regions into which one tablet of the drug A and one tablet of the drug B are put. The subsequent recessed portions 20 from numbers 9 to 16 are assigned as regions into which two tablets of drug A are put at a time. The subsequent recessed portions 20 from numbers 17 to 24 are assigned as regions into which one tablet of the drug B is put at a time.

In the embodiment described above, as illustrated in FIGS. 4 and 15 to 18, although the same drug is assigned to the recessed portions in adjacent regions in a state of being aligned to the right and along the vertical columns of the drawing, but the present invention is not limited to this configuration.

For example, the same drug may be aligned to the left, or may be grouped along the horizontal columns.

In the manual distribution members 15 adopted in the embodiment described above, the recessed portions 20 are arranged in 10 rows and 6 columns as illustrated in FIG. 4, but the numbers of rows and columns of the manual distribution members 15 are random.

The recommended number of columns is 7 columns. For example, when the first to seventh days of patient a are defined as the first to seventh columns, and the first to fourth rows are defined as morning, noon, evening, and before going to bed of the dosing timing, it is easy to distribute. Furthermore, when the fifth row is left blank and the sixth to ninth rows are continued as the morning, noon, evening, and before going to bed of dosing timing of patient b, it is easy to distribute while avoiding the error in manual distribution between patients.

The drug packaging device 1 of the embodiment described above includes the tablet supply portion 2, the manual distribution portion 3, the powder supply portion 5, and the drug packaging portion 6, and the characteristic manual distribution device (drug discharge device) 10 is adopted in the manual distribution portion 3.

It is desirable that the drug packaging device includes the tablet supply portion 2 and the powder supply portion 5 as in the embodiment described above, the manual distribution device (drug discharge device) 10 of the present invention may be adopted in a drug packaging device that does not have the tablet supply portion 2 or the like.

That is, the present invention can also be applied to a device for discharging all drugs contained in prescription information (including dispensing information obtained by processing prescription information for dispensing) input to a drug packaging device from a drug discharge device (manual distribution member).

Next, a desirable inspection device will be described. The inspection device may be built in the drug packaging device 1 or may be an independent device.

As described above, the drug packaging device 1 of the embodiment described above can prepare a strip package in which drug packages are continuous for each of the plurality of patients to take in the morning, a strip package in which drug packages are continuous for each of the plurality of patients to take at noon, a strip package in which drug packages are continuous for each of the plurality of patients to take in the evening, and a strip package in which drug packages are continuous for each of the plurality of patients to take before going to bed.

The drug packages discharged from the drug packaging device 1 are discharged by connecting the drug package to be taken in the morning by patient a, patient b, and patient c, . . . , patient i, and patient j, and the drug packages are then discharged by connecting the drug packages to be taken at noon by these patients.

The inspection device of the present embodiment includes a camera, takes pictures of the drug packages discharged from the drug packaging device 1 in the order of discharge, and identifies the packaged drugs from the stamps, shapes, and the like of the drugs. The captured video is subjected to image processing to search for drugs that are similar in shape, size, color, and the like. The drug in the drug packages is presumed to be a search ed drug.

Referring to the prescription information, it is determined whether or not the drug packaged in the drug packages is to be administered to the patient.

In addition, as illustrated in FIG. 19(a), the pharmacist also plays the captured video on a monitor or the like, and performs visual inspection.

Here, the inspection device of the present embodiment has a sorting function for rearranging images, and can display drug packages for each patient as illustrated in FIG. 19(b).

For example, as illustrated in FIG. 19(b), when patient a is selected, only the drugs taken by patient a are displayed in a state where the date of dosing and the dosing timing (morning, noon, evening) are identified.

When the prescription is for two weeks, drug packages for two weeks are displayed.

In addition, by performing a predetermined operation, it is possible to return to the display of the capturing order as illustrated in FIG. 19(a). That is, the drug packages can be displayed in the order in which the drug packages are discharged from the drug packaging device 1.

Furthermore, by designating a specific drug package for a specific patient, it is possible to check the contents of the drug packages discharged before and after the drug package.

For example, according to the prescription information, there are three tablets of the drug that patient a is scheduled to take at noon on October 7, but only two tablets are included in the actual packaging, and one tablet is missing.

As a cause of this, there is a possibility that the drug to be taken by patient a has mixed into another person's drug package.

As illustrated in FIG. 19(c), the inspection device of the present embodiment can display the discharged drug packages before and after the drug package containing the drug scheduled to be taken by patient a on October 7. Therefore, it is possible to investigate why the drug was not packaged correctly.

In addition, according to the determination of the inspection device, in a case where there is a problem such as the drugs in the drug package being different or the number being different, the screen may automatically switch to the state illustrated in FIG. 19(c).

In addition, in a case where the drugs discharged from the drug packaging device 1 at the same time are similar in shape and size, a display calling attention appears on a monitor or the like. In addition, a sound warning may be given.

Drugs with similar shapes and sizes may be difficult to determine by image processing, and the pharmacist is required to perform more careful visual checks.

Therefore, for example, it is desirable to display a warning display on one of the screens in FIG. 19.

Modification Example 1 of Divider

Next, a modification example of the divider will be described with reference to FIGS. 20 and 21. A divider 63, described below, includes a temporary accommodating member 64, as illustrated in FIG. 21. The temporary accommodating member 64 includes the blister portions 30 arranged in a matrix, similar to the divider 16 described above. The blister portions 30 correspond to the recessed portions 20 of the manual distribution member 15 one-to-one.

In the present embodiment, as illustrated in FIG. 21, an opening and closing member 65 is provided at the bottom of each blister portion 30. The opening and closing member 65 has a plate-like shape, and an intermediate portion thereof is pivotally supported by a part of the blister portion 30. The opening and closing member 65 has a plate-like shape and swings around a shaft support portion 66. The opening and closing member 65 functions as a lid member 67 on one side with the shaft support portion 66 as a boundary and functions as a power point portion 68 on the other side.

The lid member 67 of the opening and closing member 65 is located below the opening below the blister portion 30. The power point portion 68 of the opening and closing member 65 is located away from the blister portion 30.

In the opening and closing member 65, the lid member 67 is biased in the direction of blocking the bottom of the blister portion 30 by biasing means 70.

The divider 63 of the present embodiment includes a drive mechanism 71, an actuating member 72, and a clutch mechanism 73.

The actuating member 72 biases the opening and closing member 65 to swing the opening and closing member 65.

The drive mechanism 71 drives the actuating member 72. The clutch mechanism 73 is located between the drive mechanism 71 and the actuating member 72 to connect and disconnect both components.

The drive mechanism 71 is a mechanism in which racks 77a to 77f extending in the horizontal direction of the drawing are arranged in six columns in the vertical direction. A pinion 79 driven by a motor 76 is engaged with each of the racks 77a to 77f, and the racks 77a to 77f linearly move by driving the motor 76.

The actuating member 72 is a cam. Gear teeth 74 are formed on a part of the actuating member 72.

The clutch mechanism 73 includes connecting rods 73a to 73j and a solenoid 75.

In the present embodiment, six actuating members 72 are connected by the connecting rods 73a to 73j. The actuating member 72 is rotatable with respect to the connecting rods 73a to 73j. On the other hand, the actuating member 72 is axially integral with the connecting rods 73a to 73j.

The solenoid 75 is attached to each of the connecting rods 73a to 73j, and each of the connecting rods 73a to 73j moves linearly and individually by driving the solenoid 75.

In the present embodiment, the connecting rods 73a to 73j extend in the vertical direction of the drawing and are arranged in 10 columns in the horizontal direction.

Each actuating member 72 is normally on the side of the racks 77a to 77f, as illustrated in FIG. 20(b), and the gear teeth 74 of each actuating member 72 are not engaged with the racks 77a to 77f.

When the solenoid 75 located on the rightmost side of the drawing in FIG. 20(a) is energized to move the connecting rod 73a, as illustrated in FIG. 20(c), the gear teeth 74 of all actuating members 72 attached to the connecting rod 73a are engaged with the racks 77a to 77f.

In the divider 63 of the present embodiment as well, the blister portions 30 at predetermined positions can be opened in random order. As for the divider 63, it is also possible to individually discharge a drug corresponding to a predetermined recessed portion 20.

That is, the solenoids 75 drive the connecting rods 73a to 73j in the vertical columns to which the blister portion 30 to be opened belongs, and engage the racks 77a to 77f with all the actuating members 72 in the vertical columns to which the blister portion 30 to be opened belongs.

Only the racks 77a to 77f in the horizontal columns to which the blister portion 30 to be opened belongs are driven. As a result, only the specific actuating member 72 rotates, and the actuating member 72 pushes up the power point portion 68 of the opening and closing member 65 to rotate the opening and closing member 65, and lowers the lid member 67 to open the bottom of the blister portion 30.

In the divider 63 described above, the racks 77a to 77f are driven by the motors, and the connecting rods 73a to 73j are driven by the solenoids. The driving source for driving the racks 77a to 77f and the connecting rods 73a to 73j is not limited, and the racks 77a to 77f may be driven by the solenoids. In addition, the connecting rods 73a to 73j may be driven by the motors.

Modification Example 2 of Divider

In the embodiment described above, the connecting rods 73a to 73j are driven by a plurality of power sources, but the number of power sources can be reduced by using a one-way clutch or the like.

In a divider 80 illustrated in FIG. 22, one stepping motor 89 drives all the connecting rods 73a to 73j.

The divider 80 includes a rotating shaft 81 and drive side members 82 are attached to the rotating shaft 81 in a number corresponding to the connecting rods 73a to 73j. The rotating shaft 81 is rotated by a stepping motor 89.

The drive side member 82 is a disk partly provided with a stepped engaging portion 84. One side of the stepped engaging portion 84 forms an acute angle with respect to the circumference, and the other side is gently continuous with respect to the circumference. The drive side member 82 is fixed to the rotating shaft 81 with the position of the stepped engaging portion 84 gradually shifted.

A driven side member 83 is attached to each of the connecting rods 73a to 73j. The driven side member 83 is a member provided with an engaging portion 85 at the tip end. The engaging portion 85 has a hook shape bent at an acute angle.

The engaging portion 85 of the driven side member 83 is in contact with the drive side member 82.

As illustrated in FIG. 22(b), in a case where the drive side member 82 is rotated in the direction of the dashed arrow, the stepped engaging portion 84 of the drive side member 82 does not engage with the engaging portion 85.

On the other hand, when the drive side member 82 is rotated in the direction of the solid arrow as illustrated in FIG. 22(c), the stepped engaging portion 84 of the drive side member 82 engages with the engaging portion 85, and the connecting rods 73a to 73j are pulled and moved as illustrated in FIG. 22(d).

Here, since the drive side member 82 is fixed to the rotating shaft 81 with the position of the stepped engaging portion 84 gradually shifted, the stepped engaging portions 84 of a plurality of drive side members 82 are not engaged with the driven side member 83 at the same time.

In the present embodiment, the driven side member 83 in the vertical column to which the blister portion 30 to be opened belongs is engaged with the drive side member 82, and the specific connecting rods 73a to 73j are moved to engage all the actuating members 72 in the vertical columns to which the blister portions 30 to be opened belongs with the racks 77a to 77f.

Specifically, as illustrated in FIG. 22(b), the drive side member 82 is rotated in the direction of the dashed arrow so that the engaging portion 85 connected to the specific connecting rods 73a to 73j is stopped at a position fitting into the stepped engaging portion 84 of the corresponding drive side member 82. Here, since the drive side member 82 is fixed to the rotating shaft 81 with the position of the stepped engaging portion 84 gradually shifted, the engaging portion 85 that fits into the stepped engaging portion 84 of the drive side member 82 is limited to those connected to the specific connecting rods 73a to 73j.

Subsequently, as illustrated in FIGS. 22(c) and 22(d), when the drive side member 82 is rotated in the direction of the solid arrow, the stepped engaging portion 84 of the drive side member 82 engages with the engaging portion 85, and the connecting rods 73a to 73j are pulled and moved. As a result, only the specific connecting rods 73a to 73j move so that the gear teeth 74 of all the actuating members 72 attached to the connecting rods 73a to 73j engage with the racks 77a to 77f.

Other operations are the same as those of the divider 63.

Modification Example 3 of Divider

A divider 87 illustrated in FIG. 23 is configured to include a temporary accommodating member 50 and an opening forming device 90. The temporary accommodating member 50 has the same structure as that of the first embodiment, and the blister portion 30 has no bottom, and the blister portion 30 itself is normally opened.

The opening forming device 90 includes an opening identifying portion 91, an opening and closing portion 92, and an opening and closing mechanism portion 94.

The opening identifying portion 91 includes six drawer-side members 93, six winding-side members 95, and six belts 96, respectively.

The drawer-side member 93 includes a plurality of drawer pulleys 121 arranged in series on a support shaft (not illustrated). The drawer pulley 121 includes a built-in motor.

The winding-side member 95 includes a plurality of winding pulleys 122 arranged in series on a support shaft (not illustrated). The winding pulley 122 includes a built-in mainspring and is normally biased to rotate toward the winding side.

A belt 96 is wound around the winding pulley 122, and one end of the belt 96 is connected to the drawer pulley 121.

Therefore, when the drawer pulley 121 is rotated, the belt 96 wound around the winding pulley 122 is drawn out.

Each belt 96 is provided with an opening 97 at one location. Therefore, the position of the opening 97 changes according to the rotation speed of the drawer pulley 121.

The opening and closing portion 92 includes 11 swing doors 98 corresponding to the vertical columns of the blister portions 30 of the temporary accommodating member 50. An operation piece 110 protrudes from each swing door 98.

The opening and closing mechanism portion 94 includes a guide member 111 and a lifting and lowering member 112 that is regulated by the guide member 111 so as to be movable only in the vertical direction.

The lifting and lowering member 112 includes an elongated hole 113 and the operation piece 110 of the swing door 98 is engaged with the elongated hole 113.

In addition, a rotating plate 115 rotated by a motor (not illustrated) is included, and an engaging piece 116 provided on the rotating plate 115 is also engaged with the elongated hole 113 of the lifting and lowering member 112.

The rotating plate 115 is normally stopped with the engaging piece 116 at the upper position. As a result, the lifting and lowering member 112 is in the upper position, and all the opening and closing portions 92 are in a position to block the bottom of the blister portion 30.

By rotating the rotating plate 115 and moving the engaging piece 116 downward, the lifting and lowering member 112 is moved downward, and all the opening and closing portions 92 are released.

In the divider 87 of the present embodiment, one of the drawer pulleys 121 is driven to move the opening 97 of the belt 96 to below the blister portion 30 to be opened.

Thereafter, as illustrated in FIG. 23(c), the rotating plate 115 is rotated to release all the opening and closing portions 92. As a result, only the blister portion 30 in which the opening 97 of the belt 96 moves downward is substantially opened, and the drug in the blister portion 30 drops.

Modification Example 4 of Divider

The structure of the divider is random, and the divider having an opening and closing door 123 below each of the blister portions 30 as a known temporary accommodating member 117 illustrated in FIG. 24 may be used.

The temporary accommodating member 117 of this structure is periodically removed from the drug packaging device and reattached to the drug packaging device for cleaning.

Here, the temporary accommodating member 117 having the opening and closing door 123 below each of the blister portions 30 is required to be held down so that the opening and closing door 123 does not open when being attached to the drug packaging device, and skill is required to attach the temporary accommodating member 117.

The temporary accommodating member 117 of the present aspect solves this problem.

The temporary accommodating member 117 of the present aspect is provided with a closing plate insertion guide 118 on the bottom surface of the main body portion, and a closing plate 120 is attached to the bottom surface of the main body portion.

The closing plate 120 can be inserted along the closing plate insertion guide 118 and hold down the opening and closing door 123 below each of the blister portions 30 to bring the blister portions 30 into the closed state.

The temporary accommodating member 117 of the present aspect is attached to the drug packaging device with the closing plate 120 attached.

The temporary accommodating member 117 moves to the collecting hopper side after the drug is put into each of the blister portions 30 from the manual distribution member 102.

Here, there is a member that prevents the movement of the closing plate 120 on the movement path of the temporary accommodating member 117, and only the main body portion of the temporary accommodating member 117 moves toward the collecting hopper, and the closing plate 120 remains on the spot.

(Sorter Device for Strip Package)

In the related art in which drug packages are discharged by connecting in a band shape from the drug packaging device, the drug package for each patient and the drug package to be transported to each facility are discharged by connecting in the strip package shape. For example, the drugs taken by patient a for 21 days are continuously discharged in a connected state, and following this, the drugs taken by patient b for 21 days are discharged in a connected state.

In many cases, a basket is placed under a discharge portion of the drug packaging device and the strip packages are dropped into the basket.

In the drug packaging device in the related art, the strip package for patient a and the subsequent strip package for patient b are discharged from the discharge portion. In practice, the strip packages for multiple persons are discharged and multiple strip packages are mixed in the same basket.

Therefore, the operator is required to arrange the strip packages. However, the operation of arranging the strip packages is troublesome, and improvement has been desired.

As a measure for solving this problem, providing a sorter device 130 as illustrated in FIG. 25 is recommended.

The sorter device 130 includes a plurality of guide portions 132 and 133. Although there are two guide portions 132 and 133 in the present embodiment, the number of guide portions 132 and 133 is random. In addition, each of the guide portions 132 and 133 is provided with package body holding means (not illustrated). The package body holding means sandwiches and holds a part of a package body.

As illustrated in FIG. 25, the sorter device 130 is installed in the vicinity of the drug package discharge port 131 of the drug packaging device, and is lifted and lowered by lifting and lowering means (not illustrated).

When sorting the strip package by the sorter device 130, a first guide portion 132 on the lower portion side is moved to the position of the drug package discharge port 131 as illustrated in FIG. 25 (b).

For example, when the drug package for patient a is discharged from the drug package discharge port 131, a package strip 138 for patient a hangs down while being in contact with the first guide portion 132.

When all the drugs for patient a are packaged, the package strip 138 is cut in the drug packaging device, and an end portion of the package strip 138 is held by the first guide portion 132 by the package body holding means.

In the present embodiment, since there are two guide portions 132 and 133, a subsequent package strip for patient c is discharged from the drug package discharge port 131 as it is.

(Measures Against Loss of Packaging Paper)

Figure 26:
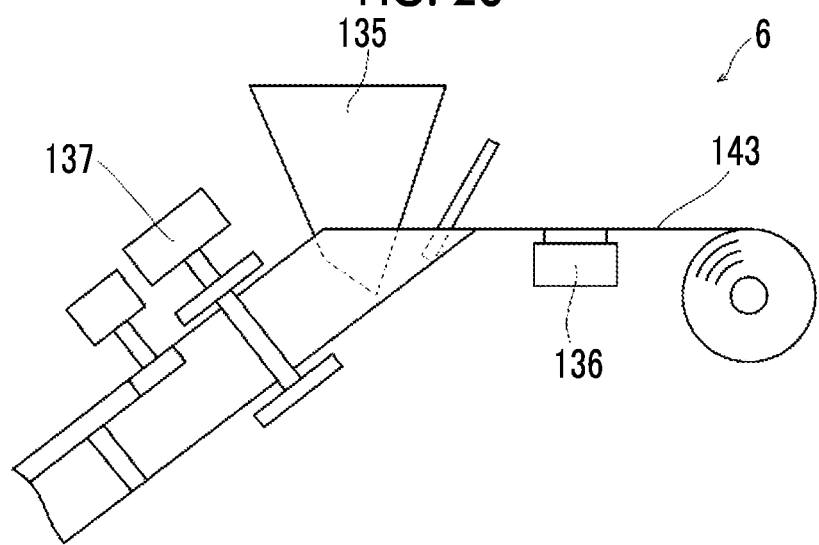
FIG. 26 is a mechanism diagram of a packaging unit of the drug discharge device.
Figures 28, 29:
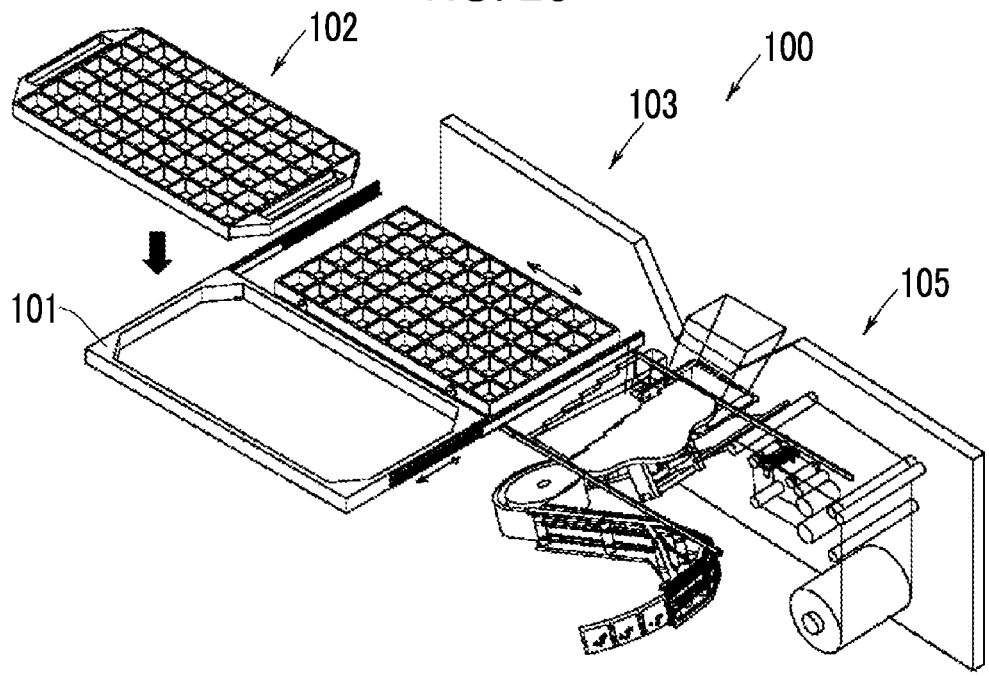
FIG. 28 is a perspective view of a manual distribution device adopted in a drug packaging device in the related art.
FIG. 29 is a front view of a strip package in which drug packages are continuous according to dosing timing.

For example, in a case where the drug packaging portion 6 having the layout as illustrated in FIG. 26 is adopted, there may be a region required to be discarded in a part of a packaging paper 143 when the package strip is switched.

The drug packaging portion 6 illustrated in FIG. 26 includes a printer 136 on the upstream side of a hopper 135 and a heater roller 137 on the downstream side of the hopper 135.

In the drug packaging portion 6, the drug is supplied to the packaging paper 143 from the hopper 135 after necessary printing is performed on the packaging paper 143 by the printer 136. In this state, the packaging paper 143 moves downstream side and is formed into an individual bag by the heater rollers 137.

For example, assuming that the drugs taken by patient a for 21 days are continuously discharged, and following this, the drugs taken by patient b for 21 days are discharged, since the last drug for patient a is supplied from hopper 135 to packaging paper 143, and the first drug for patient b is subsequently supplied to packaging paper 143, the drugs are continuously supplied to the packaging paper 143, and the packaging paper 143 is not wasted.

On the other hand, when the supply of drugs from the hopper 135 stops after the drugs to be taken by patient a for 21 days are continuously discharged, the packaging paper 143 is wasted.

That is, when the drug for patient a is supplied to the packaging paper 143, the packaging paper 143 is moved to the position of the heater roller 137 and formed into a bag shape, and when the packaging paper 143 is moved to the position of the heater roller 137, the subsequent packaging paper 143 is pulled to move to below the hopper 135 and the position of the printer 136.

However, the drug is not supplied to the packaging paper 143 reached the hopper 135. In addition, nothing is printed on the packaging paper 143 reached the position of the printer 136. Therefore, the packaging paper 143 in the region from the printer 136 to the heater roller 137 is wasted.

As a measure for solving this problem, in a case where a series of drug packages is ended and the information for the next drug package is not input, the drug package at or near the last is stopped, and a next prescription to be sent to the drug packaging device is waited for a certain period of time.

In a case where the next prescription to be processed is sent within a certain period of time, drug package is resumed. For example, in a case where a prescription for patient b is required to be processed following a prescription for patient a, the drug package for the remaining patient a is resumed, and following this, the drug package for patient b is performed.

In a case where the next prescription to be processed is not sent within a certain period of time, the remaining drug package for patient a is resumed, and the drug package for patient a is completed.

The medication calendar described above is a calendar provided with a drug accommodating portion 141 for accommodating a drug.

As illustrated in FIG. 27(a), a representative medication calendar 140 includes four drug accommodating portions 141 arranged below each date. Each of the four drug accommodating portions 141 corresponds to the timing of taking (usage), and for example, "morning", "noon", "evening", and "before going to bed" are displayed.

Drugs corresponding to the timing of taking are accommodated in the drug accommodating portion 141 of the medication calendar (drug calendar) 140. When it is the timing of taking, the drug is taken out from the corresponding drug accommodating portion 141 and taken.

In normal, the drug accommodating portion 141 is pocket-shaped. Therefore, dust 145 may accumulate at the bottom of the drug accommodating portion 141. In addition, the bottom of the drug accommodating portion 141 is often angular, and it may be difficult to remove dust from nook portions.

As a measure for solving this problem, it is recommended to use a cleaning tool 150 as illustrated in FIG. 27(b).

The cleaning tool 150 is an attachment attached to the tip end of a vacuum cleaner. The cleaning tool 150 has a rectangular parallelepiped external shape. The front wall and rear wall of the cleaning tool 150 are wide and the side walls are narrow.

The interior of the cleaning tool 150 is hollow and includes an opening 152 at a corner portion on the tip end side.

In addition, brushes 151 are attached to the front wall, rear wall, and bottom wall of the cleaning tool 150. The brush 151 is planar and thin, and is attached to the main body portion of the cleaning tool 150 by adhesive means (not illustrated).

The cleaning tool 150 is attached to a vacuum cleaner (not illustrated). As illustrated in FIG. 27(c), the cleaning tool 150 is inserted into the drug accommodating portion 141 of the medication calendar 140, and the cleaning tool 150 is moved in the take-in and take-out direction in the drug accommodating portion 141.

As a result, the inner surface of the drug accommodating portion 141 is rubbed with the brush 151 to remove dust or dirt adhering to the inner surface of the drug accommodating portion 141. In addition, the removed dust or dirt is sucked through the opening 152. Especially in the present embodiment, since the cleaning tool 150 includes the opening 152 at the corner portion on the tip end side, the nook portions of the drug accommodating portion 141 where dust is likely to accumulate can also be cleaned cleanly.

It is desirable that the brush 151 is replaceable.

REFERENCE SIGNS LIST

1: drug packaging device
6: drug packaging portion
10: manual distribution device (drug discharge device)
11: display device
12: display screen
15: manual distribution member
16: divider (discharge means)
18: simulated chart (guidance means)
20: recessed portion
22: indicator lamp (indicating means or guidance means)
30: blister portion
40: control device
50: temporary accommodating member
51: bottom constituting member
55: entire closed region
56: openable region
58: moving floor member
61: drop opening
62: drug

The invention claimed is:
1. A drug discharge device (10) comprising:
a manual distribution member (15) that includes a plurality of recessed portions (20) in which a solid drug is distributed;

discharge means (16) that discharges the drug distributed in the recessed portions (20) to a downstream side directly or via another member; and a control device (40) that controls the discharge means (16), wherein the discharge means (16) is capable of individually discharging a drug corresponding to a predetermined recessed portion (20), the control device (40) assigns the same drug to the recessed portions (20) in adjacent regions based on prescription information including information on a drug to be provided to a plurality of patients or one patient, and the discharge means (16) discharges the drugs in a predetermined order.

2. The drug discharge device (10) according to claim 1, wherein the recessed portion (20) is distributed with one or a plurality of drugs for one dose, the drug for one dose is one type or a plurality of types of drugs, and the drug having the same type and number is assigned to the recessed portions (20) in adjacent regions.

3. The drug discharge device (10) according to claim 1, further comprising:

display means (11), wherein the display means (11) is capable of displaying a simulated chart (18) simulating an arrangement of the recessed portions (20), and information related to a drug required to be distributed is displayed on the simulated chart (18) and/or the same screen as the simulated chart (18).

4. The drug discharge device (10) according to claim 3, wherein a uniform mark is displayed on the recessed portion (20) in which the same drug is required to be put in the simulated chart (18).

5. The drug discharge device (10) according to claim 1, wherein the manual distribution member (15) includes indicating means (22) that indicates a recessed portion (20) in which a drug is required to be put.

6. The drug discharge device (10) according to claim 1, wherein a divider (16) is disposed below the manual distribution member (15), the divider (16) includes a temporary accommodating member (50) and a bottom constituting member (51), the temporary accommodating member (50) includes a blister portion (30), and the blister portion (30) corresponds to the recessed portion (20) of the manual distribution member (15) and a bottom side is opened, the bottom constituting member (51) is capable of opening and closing a specific portion to form a drop opening (61), and the temporary accommodating member (50) and the bottom constituting member (51) are movable relative to each other, and at least one of the temporary accommodating member (50) and the bottom constituting member (51) is capable of being moved to move a specific blister portion to a position (30) where the drop opening (61) of the bottom constituting member (51) is formed.

7. The drug discharge device (10) according to claim 6, wherein the bottom constituting member (51) has an entire closed region (55) and an openable region (56), the openable region (56) is configured by arranging moving floor members (58) having narrow flat surfaces, and the moving floor member (58) is individually capable of moving in parallel, and the moving floor member (58) is moved in parallel to form the drop opening (61) between the entire closed region (55) and the moving floor member (58).

8. The drug discharge device (10) according to claim 1, wherein a bottom side of the recessed portion (20) of the manual distribution member (15) is opened, and a bottom constituting member (51) is provided below the manual distribution member (15), the bottom constituting member (51) is capable of opening and closing a specific portion to form a drop opening (61), and the manual distribution member (15) and the bottom constituting member (51) are movable relative to each other, and at least one of the manual distribution member (15) and the bottom constituting member (51) is capable of being moved to move a specific recessed portion (20) to a position where the drop opening (61) of the bottom constituting member (51) is formed.

9. A drug packaging device (1) comprising:

the drug discharge device (10) according to claim 1; and a packaging device that packages a drug discharged from the drug discharge device (10).

10. A drug discharge device (10) comprising:

a manual distribution member (15) that includes a plurality of recessed portions (20) in which a solid drug is distributed; and discharge means (16) that discharges the drug distributed in the recessed portions (20) to a downstream side directly or via another member, wherein the recessed portion (20) is distributed with one or a plurality of drugs for one dose, and the drug discharge device (10) further comprises recessed portion determining means (40) that determines a recessed portion (20) required to be distributed based on a type of drug; and guidance means (22) that guides a determined recessed portion (20).

11. A drug discharge device (10) comprising:

a plurality of drug feeders;

a manual distribution member (15) that includes a plurality of recessed portions (20) in which a solid drug is distributed; and discharge means (16) that discharges the drug distributed in the recessed portions (20) to a downstream side directly or via another member, wherein a drug cassette capable of being filled with a plurality of drugs is attached to the drug feeder, and the drug feeder discharges the drug from the drug cassette, the recessed portion (20) is distributed with one or a plurality of drugs for one dose, and the drug discharge device (10) further comprises recessed portion determining means (40) that distinguishes between a drug capable of being discharged from the drug feeder and a drug not capable of being discharged from the drug feeder, and determines a recessed portion (20) required to be distributed based on a type of drug when discharging the drug not capable of being discharged via the manual distribution member (15).

* * * * *